United States Patent
Boyer et al.

(10) Patent No.: US 7,928,227 B2
(45) Date of Patent: Apr. 19, 2011

(54) 2-OXO-1,3,5-PERHYDROTRIAZAPINE DERIVATIVES USEFUL IN THE TREATMENT OF HYPER-PROLIFERATIVE, ANGIOGENESIS, AND INFLAMMATORY DISORDERS

(75) Inventors: Stephen Boyer, Fairfield, CT (US); Jacques Dumas, Bethany, CT (US); Barton Phillips, New Haven, CT (US); William J. Scott, Guildford, CT (US); Roger A. Smith, Madison, CT (US); Jianqing Chen, New Haven, CT (US); Benjamin Jones, Hamden, CT (US); Gan Wang, Wallingford, CT (US)

(73) Assignee: Bayer Healthcare LLC, Tarrytown, NY (US)

( * ) Notice: Subject to any disclaimer, the term of this patent is extended or adjusted under 35 U.S.C. 154(b) by 0 days.

(21) Appl. No.: 10/788,405

(22) Filed: Mar. 1, 2004

(65) Prior Publication Data
US 2005/0032798 A1  Feb. 10, 2005

Related U.S. Application Data

(60) Provisional application No. 60/450,323, filed on Feb. 28, 2003, provisional application No. 60/450,324, filed on Feb. 28, 2003, provisional application No. 60/450,348, filed on Feb. 28, 2003.

(51) Int. Cl.
| | |
|---|---|
| C07D 251/08 | (2006.01) |
| C07D 401/04 | (2006.01) |
| C07D 401/14 | (2006.01) |
| C07D 403/04 | (2006.01) |
| C07D 403/14 | (2006.01) |
| A61K 31/53 | (2006.01) |
| A61P 19/02 | (2006.01) |

(52) U.S. Cl. ............... 544/220; 514/241; 514/231.5; 544/113

(58) Field of Classification Search ............ 544/220; 514/241
See application file for complete search history.

(56) References Cited

U.S. PATENT DOCUMENTS

| | | | |
|---|---|---|---|
| 3,505,057 | A | 4/1970 | Luckenbaugh |
| 3,505,323 | A | 4/1970 | Luckenbaugh |
| 3,698,886 | A | 10/1972 | Chupp |
| 3,860,593 | A | 1/1975 | Krenzer |
| 3,899,489 | A | 8/1975 | Horlein et al. |
| 3,914,224 | A | 10/1975 | Jewell |
| 4,152,516 | A | 5/1979 | Hardies |
| 4,624,698 | A | 11/1986 | Aoki et al. |
| 4,734,414 | A | 3/1988 | Kim et al. |
| 4,767,858 | A | 8/1988 | Kim et al. |
| 4,868,178 | A | 9/1989 | Katoh et al. |
| 5,240,926 | A | 8/1993 | Heinemann et al. |
| 7,038,045 | B2 | 5/2006 | Guzi et al. |
| 7,091,203 | B2 | 8/2006 | Niewohner et al. |
| 7,173,032 | B2 | 2/2007 | Timmer et al. |
| 7,208,597 | B2 | 4/2007 | Holzl et al. |
| 2006/0106019 | A1 | 5/2006 | Bernard |
| 2006/0128707 | A1 | 6/2006 | Inoue et al. |
| 2006/0148802 | A1 | 7/2006 | Haning et al. |
| 2007/0099874 | A1 | 5/2007 | Timmer et al. |
| 2007/0142310 | A1 | 6/2007 | Daifuku et al. |

FOREIGN PATENT DOCUMENTS

| | | | |
|---|---|---|---|
| EP | 1 119306 | * | 4/2002 |
| JP | 401132580 A | | 5/1989 |
| WO | WO 9849150 A1 | * | 11/1998 |

OTHER PUBLICATIONS

Cecil Textbook of Medicine, edited by Bennet, J.C., and Plum F., 20th edition, vol. 1, 1004-1010, 1996.*
Mass, R. D., Int. J. Radiation Oncology Bio. Phys.vol. 58(3): 932-940, 2004.*
Fabbro et al. Pharmacology & therapeutics 93, 79-98, 2002.*
Turner et al., Current Pharmaceutical Design. 2, 209-224, 1996.*
Sugar et al., Diagn. Microbiol. Infect. Dis. 21: 129-133, 1995.*
Snyder et al., J. Med. Liban 48(4): 208-214, 2000.*

* cited by examiner

*Primary Examiner* — Venkataraman Balasubramanian
(74) *Attorney, Agent, or Firm* — Millen, White, Zelano & Branigan, P.C.

(57) ABSTRACT

This invention relates to novel diaryl ureas, pharmaceutical compositions containing such compounds and the use of those compounds or compositions for treating hyper-proliferative and angiogenesis disorders, as a sole agent or in combination with cytotoxic therapies.

28 Claims, No Drawings

2-OXO-1,3,5-PERHYDROTRIAZAPINE DERIVATIVES USEFUL IN THE TREATMENT OF HYPER-PROLIFERATIVE, ANGIOGENESIS, AND INFLAMMATORY DISORDERS

RELATED APPLICATIONS

This application claims priority to Ser. No. 60/450,323, filed Feb. 28, 2003, Ser. No. 60/450,324 filed Feb. 28, 2003 and Ser. No. 60/450,348 filed Feb. 28, 2003 which are incorporated by reference herein.

FIELD OF THE INVENTION

This invention relates to novel compounds, pharmaceutical compositions containing such compounds and the use of those compounds or compositions for treating hyper-proliferative and angiogenesis disorders, as a sole agent or in combination with other active ingredients, e.g., cytotoxic therapies.

BACKGROUND OF THE INVENTION

Activation of the ras signal transduction pathway indicates a cascade of events that have a profound impact on cellular proliferation, differentiation, and transformation. Raf kinase, a downstream effector of ras, is recognized as a key mediator of these signals from cell surface receptors to the cell nucleus (Lowy, D. R.; Willumsen, B. M. *Ann. Rev. Biochem.* 1993, 62, 851; Bos, J. L. *Cancer Res* .1989, 49, 4682). It has been shown that inhibiting the effect of active ras by inhibiting the raf kinase signaling pathway by administration of deactivating antibodies to raf kinase or by co-expression of dominant negative raf kinase or dominant negative MEK, the substrate of raf kinase, leads to the reversion of transformed cells to the normal growth phenotype (see: Daum et al. *Trends Biochem. Sci.* 1994, 19, 474-80; Fridman et al. *J. Biol. Chem.* 1994, 269, 30105-8. Kolch et al. (*Nature* 1991, 349, 426-28) have further indicated that inhibition of raf expression by antisense RNA blocks cell proliferation in membrane-associated oncogenes. Similarly, inhibition of raf kinase (by antisense oligodeoxynucleotides) has been correlated in vitro and in vivo with inhibition of the growth of a variety of human tumor types (Monia et al., *Nat. Med.* 1996, 2, 668-75). Some examples of small molecule inhibitors of Raf kinase activity are important agents for the treatment of cancer. (Naumann, U.; Eisenmann-Tappe, I.; Rapp, U. R. *Recent Results Cancer Res.* 1997, 143, 237; Monia, B. P.; Johnston, J. F.; Geiger, T.; Muller, M.; Fabbro, D. *Nature Medicine* 1996, 2, 668).

To support progressive tumor growth beyond the size of 1-2 mm$^3$, it is recognized that tumor cells require a functional stroma, a support structure consisting of fibroblast, smooth muscle cells, endothelial cells, extracellular matrix proteins, and soluble factors (Folkman, J., *Semin Oncol*, 2002. 29(6 Suppl 16), 15-8). Tumors induce the formation of stromal tissues through the secretion of soluble growth factors such as PDGF and transforming growth factor-beta (TGF-beta), which in turn stimulate the secretion of complimentary factors by host cells such as fibroblast growth factor (FGF), epidermal growth factor (EGF), and vascular endothelial growth factor (VEGF). These stimulatory factors induce the formation of new blood vessels, or angiogenesis, which brings oxygen and nutrients to the tumor and allows it to grow and provides a route for metastasis. It is believed some therapies directed at inhibiting stroma formation will inhibit the growth of epithelial tumors from a wide variety of histological types. (George, D. *Semin Oncol*, 2001. 28(5 Suppl 17), 27-33; Shaheen, R. M., et al., *Cancer Res*, 2001. 61(4), 1464-8; Shaheen, R. M., et al. *Cancer Res*, 1999. 59(21), 5412-6). However, because of the complex nature and the multiple growth factors involved in angiogenesis process and tumor progression, an agent targeting a single pathway may have limited efficacy. It is desirable to provide treatment against a number of key signaling pathways utilized by tumors to induce angiogenesis in the host stroma. These include PDGF, a potent stimulator of stroma formation (Ostman, A. and C. H. Heldin, *Adv Cancer Res*, 2001, 80, 1-38), FGF, a chemoattractant and mitogen for fibroblasts and endothelial cells, and VEGF, a potent regulator of vascularization.

PDGF is another key regulator of stromal formation which is secreted by many tumors in a paracrine fashion and is believed to promote the growth of fibroblasts, smooth muscle and endothelial cells, promoting stroma formation and angiogenesis. PDGF was originally identified as the v-sis oncogene product of the simian sarcoma virus (Heldin, C. H., et al., *J Cell Sci Suppl*, 1985, 3, 65-76). The growth factor is made up of two peptide chains, referred to as A or B chains which share 60% homology in their primary amino acid sequence. The chains are disulfide cross linked to form the 30 kDa mature protein composed of either M, BB or AB homo- or heterodimers. PDGF is found at high levels in platelets, and is expressed by endothelial cells and vascular smooth muscle cells. In addition, the production of PDGF is up regulated under low oxygen conditions such as those found in poorly vascularized tumor tissue (Kourembanas, S., et al., *Kidney Int*, 1997, 51(2), 438-43). PDGF binds with high affinity to the PDGF receptor, a 1106 amino acid 124 kDa transmembrane tyrosine kinase receptor (Heldin, C. H., A. Ostman, and L. Ronnstrand, *Biochim Biophys Acta*, 1998. 1378(1), 79-113). PDGFR is found as homo- or heterodimer chains which have 30% homology overall in their amino acid sequence and 64% homology between their kinase domains (Heldin, C. H., et al. *Embo J*, 1988, 7(5), 1387-93). PDGFR is a member of a family of tyrosine kinase receptors with split kinase domains that includes VEGFR2 (KDR), VEGFR3 (Flt4), c-Kit, and FLT3. The PDGF receptor is expressed primarily on fibroblast, smooth muscle cells, and pericytes and to a lesser extent on neurons, kidney mesangial, Leydig, and Schwann cells of the central nervous system. Upon binding to the receptor, PDGF induces receptor dimerization and undergoes auto- and trans-phosphorylation of tyrosine residues which increase the receptors' kinase activity and promotes the recruitment of downstream effectors through the activation of SH2 protein binding domains. A number of signaling molecules form complexes with activated PDGFR including PI-3-kinase, phospholipase C-gamma, src and GAP (GTPase activating protein for p21-ras) (Soskic, V., et al. *Biochemistry*, 1999, 38(6), 1757-64). Through the activation of PI-3-kinase, PDGF activates the Rho signaling pathway inducing cell motility and migration, and through the activation of GAP, induces mitogenesis through the activation of p21-ras and the MAPK signaling pathway.

In adults, it is believed the major function of PDGF is to facilitate and increase the rate of wound healing and to maintain blood vessel homeostasis (Baker, E.A. and D. J. Leaper, *Wound Repair Regen*, 2000. 8(5), 392-8; Yu, J., A. Moon, and H. R. Kim, *Biochem Biophys Res Commun*, 2001. 282(3), 697-700). PDGF is found at high concentrations in platelets and is a potent chemoattractant for fibroblast, smooth muscle cells, neutrophils and macrophages. In addition to its role in wound healing PDGF is known to help maintain vascular homeostasis. During the development of new blood vessels, PDGF recruits pericytes and smooth muscle cells that are needed for the structural integrity of the vessels. PDGF is thought to play a similar role during tumor neovascularization. As part of its role in angiogenesis PDGF controls interstitial fluid pressure, regulating the permeability of vessels through its regulation of the interaction between connective tissue cells and the extracellular matrix. Inhibiting PDGFR activity can lower interstitial pressure and facilitate the influx of cytotoxics into tumors improving the anti-tumor efficacy of these agents (Pietras, K., et al. *Cancer Res*, 2002. 62(19), 5476-84; Pietras, K., et al. *Cancer Res*, 2001. 61(7), 2929-34).

PDGF can promote tumor growth through either the paracrine or autocrine stimulation of PDGFR receptors on stromal cells or tumor cells directly, or through the amplification of the receptor or activation of the receptor by recombination. Over expressed PDGF can transform human melanoma cells and keratinocytes (Forsberg, K., et al. *Proc Natl Acad Sci USA*., 1993. 90(2), 393-7; Skobe, M. and N. E. Fusenig, *Proc Natl Acad Sci USA*, 1998. 95(3), 1050-5), two cell types that do not express PDGF receptors, presumably by the direct effect of PDGF on stroma formation and induction of angiogenesis. This paracrine stimulation of tumor stroma is also observed in carcinomas of the colon, lung, breast, and prostate (Bhardwaj, B., et al. *Clin Cancer Res*, 1996, 2(4), 773-82; Nakanishi, K., et al. *Mod Pathol*, 1997, 10(4), 341-7; Sundberg, C., et al. *Am J Pathol*, 1997, 151(2), 479-92; Lindmark, G., et al. *Lab Invest*, 1993, 69(6), 682-9; Vignaud, J. M., et al, *Cancer Res*, 1994, 54(20), 5455-63) where the tumors express PDGF, but not the receptor. The autocrine stimulation of tumor cell growth, where a large faction of tumors analyzed express both the ligand PDGF and the receptor, has been reported in glioblastomas (Fleming, T. P., et al. *Cancer Res*, 1992, 52(16), 4550-3), soft tissue sarcomas (Wang, J., M. D. Coltrera, and A. M. Gown, *Cancer Res*, 1994, 54(2), 560-4) and cancers of the ovary (Henriksen, R., et al. *Cancer Res*, 1993, 53(19), 4550-4), prostate (Fudge, K., C. Y. Wang, and M. E. Stearns, *Mod Pathol*, 1994, 7(5), 549-54), pancreas (Funa, K., et al. *Cancer Res*, 1990, 50(3), 748-53) and lung (Antoniades, H. N., et al., *Proc Natl Acad Sci USA*, 1992, 89(9), 3942-6). Ligand independent activation of the receptor is found to a lesser extent but has been reported in chronic myelomonocytic leukemia (CMML) where the a chromosomal translocation event forms a fusion protein between the Ets-like transcription factor TEL and the PDGF receptor. In addition, activating mutations in PDGFR have been found in gastrointestinal stromal tumors in which c-Kit activation is not involved (Heinrich, M. C., et al., *Science*, 2003, 9, 9). Certain PDGFR inhibitors will interfere with tumor stromal development and are believed to inhibit tumor growth and metastasis.

Another major regulator of angiogenesis and vasculogenesis in both embryonic development and some angiogenic-dependent diseases is vascular endothelial growth factor (VEGF; also called vascular permeability factor, VPF). VEGF represents a family of isoforms of mitogens existing in homodimeric forms due to alternative RNA splicing. The VEGF isoforms are reported to be highly specific for vascular endothelial cells (for reviews, see: Farrara et al. *Endocr. Rev.* 1992, 13, 18; Neufield et al. *FASEB J*. 1999, 13, 9).

VEGF expression is reported to be induced by hypoxia (Shweiki et al. *Nature* 1992, 359, 843), as well as by a variety of cytokines and growth factors, such as interleukin-1, interleukin-6, epidermal growth factor and transforming growth factor.

To date, VEGF and the VEGF family members have been reported to bind to one or more of three transmembrane receptor tyrosine kinases (Mustonen et al. *J. Cell Biol.*, 1995, 129, 895), VEGF receptor-1 (also known as flt-1 (fms-like tyrosine kinase-1)), VEGFR-2 (also known as kinase insert domain containing receptor (KDR); the murine analogue of KDR is known as fetal liver kinase-1 (flk-1)), and VEGFR-3 (also known as flt4). KDR and flt-1 have been shown to have different signal transduction properties (Waltenberger et al. *J. Biol. Chem*. 1994, 269, 26988); Park et al. *Oncogene* 1995, 10, 135). Thus, KDR undergoes strong ligand-dependant tyrosine phosphorylation in intact cells, whereas flt-1 displays a weak response. Thus, binding to KDR is believed to be a critical requirement for induction of the full spectrum of VEGF-mediated biological responses.

In vivo, VEGF plays a central role in vasculogenesis, and induces angiogenesis and permeabilization of blood vessels. Deregulated VEGF expression contributes to the development of a number of diseases that are characterized by abnormal angiogenesis and/or hyperpermeability processes. It is believed regulation of the VEGF-mediated signal transduction cascade by some agents can provide a useful mode for control of abnormal angiogenesis and/or hyperpermeability processes.

Angiogenesis is regarded as an important prerequisite for growth of tumors beyond about 1-2 mm. Oxygen and nutrients may be supplied to cells in tumor smaller than this limit through diffusion. However, it is believed every tumor is dependent on angiogenesis for continued growth after it has reached a certain size. Tumorigenic cells within hypoxic regions of tumors respond by stimulation of VEGF production, which triggers activation of quiescent endothelial cells to stimulate new blood vessel formation. (Shweiki et al. *Proc. Nat'l. Acad. Sci*., 1995, 92, 768). In addition, VEGF production in tumor regions where there is no angiogenesis may proceed through the ras signal transduction pathway (Grugel et al. *J. Biol. Chem.*, 1995, 270, 25915; Rak et al. *Cancer Res*. 1995, 55, 4575). In situ hybridization studies have demonstrated VEGF mRNA is strongly upregulated in a wide variety of human tumors, including lung (Mattern et al. *Br. J. Cancer* 1996, 73, 931), thyroid (Viglietto et al. *Oncogene* 1995, 11, 1569), and breast (Brown et al. *Human Pathol*. 1995, 26, 86), gastrointestinal tract (Brown et al. *Cancer Res*. 1993, 53, 4727; Suzuki et al. *Cancer Res*. 1996, 56, 3004), kidney and bladder (Brown et al. *Am. J. Pathol*. 1993, 1431, 1255), ovary (Olson et al. *Cancer Res*. 1994, 54, 1255), and cervical (Guidi et al. *J. Nat'l Cancer Inst*. 1995, 87, 12137) carcinomas, as well as angiosacroma (Hashimoto et al. *Lab. Invest*. 1995, 73, 859) and several intracranial tumors (Plate et al. *Nature* 1992, 359, 845; Phillips et al. *Int. J. Oncol*. 1993, 2, 913; Berkman et al. *J. Clin. Invest.*, 1993, 91, 153). Neutralizing monoclonal antibodies to KDR have been shown to be efficacious in blocking tumor angiogenesis (Kim et al. *Nature* 1993, 362, 841; Rockwell et al. *Mol. Cell. Differ*. 1995, 3, 315).

Over expression of VEGF, for example under conditions of extreme hypoxia, can lead to intraocular angiogenesis, resulting in hyperproliferation of blood vessels, leading eventually to blindness. Such a cascade of events has been observed for a number of retinopathies, including diabetic retinopathy, ischemic retinal-vein occlusion, and retinopathy of prematurity (Aiello et al. *New Engl. J. Med*. 1994, 331, 1480; Peer et al. *Lab. Invest*. 1995, 72, 638), and age-related macular degeneration (AMD; see, Lopez et al. *Invest. Opththalmol. Vis. Sci*. 1996, 37, 855).

In rheumatoid arthritis (RA), the in-growth of vascular pannus may be mediated by production of angiogenic factors. Levels of immunoreactive VEGF are high in the synovial fluid of RA patients, while VEGF levels were low in the synovial fluid of patients with other forms of arthritis of with degenerative joint disease (Koch et al. *J. Immunol*. 1994, 152, 4149). The angiogenesis inhibitor AGM-170 has been shown to prevent neovascularization of the joint in the rat collagen arthritis model (Peacock et al. *J. Exper. Med.* 1992, 175, 1135).

Increased VEGF expression has also been shown in psoriatic skin, as well as bullous disorders associated with subepidermal blister formation, such as bullous pemphigoid, erythema multiforme, and dermatitis herpetiformis (Brown et al. *J. Invest. Dermatol.* 1995, 104, 744).

The vascular endothelial growth factors (VEGF, VEGF-C, VEGF-D) and their receptors (VEGFR2, VEGFR3) are not only key regulators of tumor angiogenesis, but also lymphangiogenesis. VEGF, VEGF-C and VEGF-D are expressed in most tumors, primarily during periods of tumor growth and, often at substantially increased levels. VEGF expression is stimulated by hypoxia, cytokines, oncogenes such as ras, or by inactivation of tumor suppressor genes (McMahon, G. *Oncologist* 2000, 5(Suppl. 1), 3-10; McDonald, N. Q.; Hendrickson, W. A. *Cell* 1993, 73, 421-424).

The biological activities of the VEGFs are mediated through binding to their receptors. VEGFR3 (also called Flt-4) is predominantly expressed on lymphatic endothelium in normal adult tissues. VEGFR3 function is needed for new lymphatic vessel formation, but not for maintenance of the pre-existing lymphatics. VEGFR3 is also upregulated on blood vessel endothelium in tumors. Recently VEGF-C and VEGF-D, ligands for VEGFR3, have been identified as regulators of lymphangiogenesis in mammals. Lymphangiogenesis induced by tumor-associated lymphangiogenic factors could promote the growth of new vessels into the tumor, providing tumor cells access to systemic circulation. Cells that invade the lymphatics could find their way into the bloodstream via the thoracic duct. Tumor expression studies have allowed a direct comparison of VEGF-C, VEGF-D and VEGFR3 expression with clinicopathological factors that relate directly to the ability of primary tumors to spread (e.g., lymph node involvement, lymphatic invasion, secondary metastases, and disease-free survival). In many instances, these studies demonstrate a statistical correlation between the expression of lymphangiogenic factors and the ability of a primary solid tumor to metastasize (Skobe, M. et al. *Nature Med.* 2001, 7(2), 192-198; Stacker, S. A. et al. *Nature Med.* 2001, 7(2), 186-191; Makinen, T. et al. *Nature Med.* 2001, 7(2), 199-205; Mandriota, S. J. et al. *EMBO J.* 2001, 20(4), 672-82; Karpanen, T. et al. *Cancer Res.* 2001, 61(5), 1786-90; Kubo, H. et al. *Blood* 2000, 96(2), 546-53).

Inhibition of the mitogen-activated protein kinase (MAPK) p38 has been shown to inhibit both cytokine production (e.g., TNF, IL-1, IL-6, IL-8) and proteolytic enzyme production (e.g., MMP-1, MMP-3) in vitro and/or in vivo. The mitogen activated protein (MAP) kinase p38 is involved in IL-1 and TNF signaling pathways (Lee, J. C.; Laydon, J. T.; McDonnell, P. C.; Gallagher, T. F.; Kumar, S.; Green, D.; McNulty, D.; Blumenthal, M. J.; Heys, J. R.; Landvatter, S. W.; Stricker, J. E.; McLaughlin, M. M.; Siemens, I. R.; Fisher, S. M.; Livi, G. P.; White, J. R.; Adams, J. L.; Yound, P. R. *Nature* 1994, 372, 739).

Clinical studies have linked tumor necrosis factor (TNF) production and/or signaling to a number of diseases including rheumatoid arthritis (Maini. *J. Royal Coll. Physicians London* 1996, 30, 344). In addition, excessive levels of TNF have been implicated in a wide variety of inflammatory and/or immunomodulatory diseases, including acute rheumatic fever (Yegin et al. *Lancet* 1997, 349, 170), bone resorption (Pacifici et al. *J. Clin. Endocrinol. Metabol.* 1997, 82, 29), postmenopausal osteoporosis (Pacifici et al. *J. Bone Mineral Res.* 1996, 11, 1043), sepsis (Blackwell et al. *Br. J. Anaesth.* 1996, 77, 110), gram negative sepsis (Debets et al. *Prog. Clin. Biol. Res.* 1989, 308, 463), septic shock (Tracey et al. *Nature* 1987, 330, 662; Girardin et al. *New England J. Med.* 1988, 319, 397), endotoxic shock (Beutler et al. *Science* 1985, 229, 869; Ashkenasi et al. *Proc. Nat'l. Acad. Sci. USA* 1991, 88, 10535), toxic shock syndrome, (Saha et al. *J. Immunol.* 1996, 157, 3869; Lina et al. *FEMS Immunol. Med. Microbiol.* 1996, 13, 81), systemic inflammatory response syndrome (Anon. *Crit. Care Med.* 1992, 20, 864), inflammatory bowel diseases (Stokkers et al. *J. Inflamm.* 1995-6, 47, 97) including Crohn's disease (van Deventer et al. *Aliment. Pharmacol. Therapeu.* 1996, 10 (Suppl. 2), 107; van Dullemen et al. *Gastroenterology* 1995, 109, 129) and ulcerative colitis (Masuda et al. *J. Clin. Lab. Immunol.* 1995, 46, 111), Jarisch-Herxheimer reactions (Fekade et al. *New England J. Med.* 1996, 335, 311), asthma (Amrani et al. *Rev. Malad. Respir.* 1996, 13, 539), adult respiratory distress syndrome (Roten et al. *Am. Rev. Respir. Dis.* 1991, 143, 590; Suter et al. *Am. Rev. Respir. Dis.* 1992, 145, 1016), acute pulmonary fibrotic diseases (Pan et al. *Pathol. Int.* 1996, 46, 91), pulmonary sarcoidosis (Ishioka et al. *Sarcoidosis Vasculitis Diffuse Lung Dis.* 1996, 13, 139), allergic respiratory diseases (Casale et al. *Am. J. Respir. Cell Mol. Biol.* 1996, 15, 35), silicosis (Gossart et al. *J. Immunol.* 1996, 156, 1540; Vanhee et al. *Eur. Respir. J.* 1995, 8, 834), coal worker's pneumoconiosis (Borm et al. *Am. Rev. Respir. Dis.* 1988, 138, 1589), alveolar injury (Horinouchi et al. *Am. J. Respir. Cell Mol. Biol.* 1996, 14, 1044), hepatic failure (Gantner et al. *J. Pharmacol. Exp. Therap.* 1997, 280, 53), liver disease during acute inflammation (Kim et al. *J. Biol. Chem.* 1997, 272, 1402), severe alcoholic hepatitis (Bird et al. *Ann. Intern. Med.* 1990, 112, 917), malaria (Grau et al. *Immunol. Rev.* 1989, 112, 49; Taverne et al. *Parasitol. Today* 1996, 12, 290) including *Plasmodium falciparum* malaria (Perlmann et al. *Infect. Immunit.* 1997, 65, 116) and cerebral malaria (Rudin et al. *Am. J. Pathol.* 1997, 150, 257), non-insulin-dependent diabetes mellitus (NIDDM; Stephens et al. *J. Biol. Chem.* 1997, 272, 971; Ofei et al. *Diabetes* 1996, 45, 881), congestive heart failure (Doyama et al. *Int. J. Cardiol.* 1996, 54, 217; McMurray et al. *Br. Heart J.* 1991, 66, 356), damage following heart disease (Malkiel et al. *Mol. Med. Today* 1996, 2, 336), atherosclerosis (Parums et al. *J. Pathol.* 1996, 179, A46), Alzheimer's disease (Fagarasan et al. *Brain Res.* 1996, 723, 231; Aisen et al. *Gerontology* 1997, 43, 143), acute encephalitis (Ichiyama et al. *J. Neurol.* 1996, 243, 457), brain injury (Cannon et al. *Crit. Care Med.* 1992, 20, 1414; Hansbrough et al. *Surg. Clin. N. Am.* 1987, 67, 69; Marano et al. *Surg. Gynecol. Obstetr.* 1990, 170, 32), multiple sclerosis (M. S.; Coyle. *Adv. Neuroimmunol.* 1996, 6, 143; Matusevicius et al. *J. Neuroimmunol.* 1996, 66, 115) including demyelation and oligiodendrocyte loss in multiple sclerosis (Brosnan et al. *Brain Pathol.* 1996, 6, 243), advanced cancer (MucWierzgon et al. *J. Biol. Regulators Homeostatic Agents* 1996, 10, 25), lymphoid malignancies (Levy et al. *Crit. Rev. Immunol.* 1996, 16, 31), pancreatitis (Exley et al. *Gut* 1992, 33, 1126) including systemic complications in acute pancreatitis (McKay et al. *Br. J. Surg.* 1996, 83, 919), impaired wound healing in infection inflammation and cancer (Buck et al. *Am. J. Pathol.* 1996, 149, 195), myelodysplastic syndromes (Raza et al. *Int. J. Hematol.* 1996, 63, 265), systemic lupus erythematosus (Maury et al. *Arthritis Rheum.* 1989, 32, 146), biliary cirrhosis (Miller et al. *Am. J. Gasteroenterolog.* 1992, 87, 465), bowel necrosis (Sun et al. *J. Clin. Invest.* 1988, 81, 1328), psoriasis (Christophers. *Austr. J. Dermatol.* 1996, 37, S4), radiation injury (Redlich et al. *J. Immunol.* 1996, 157, 1705), and toxicity following administration of monoclonal antibodies such as OKT3 (Brod et al. *Neurology* 1996, 46, 1633). TNF levels have also been related to host-versus-graft reactions (Piguet et al. *Immunol. Ser.* 1992, 56, 409) including ischemia reperfusion injury (Colletti et al. *J. Clin. Invest.* 1989, 85, 1333) and allograft rejections including those of the kidney (Maury et al. *J. Exp. Med.* 1987, 166, 1132), liver (Imagawa et al. *Transplantation* 1990, 50, 219), heart (Bolling et al. *Transplantation* 1992, 53, 283), and skin (Stevens et al. *Transplant. Proc.* 1990, 22, 1924), lung allograft rejection (Grossman et al. *Immunol. Allergy Clin. N. Am.* 1989, 9, 153) including chronic lung allograft rejection (obliterative bronchitis; LoCicero et al. *J. Thorac. Cardiovasc. Surg.* 1990, 99, 1059), as well as complications due to total hip replacement (Cirino et al. *Life Sci.* 1996, 59, 86). TNF has also been linked to infectious diseases (review: Beutler et al. *Crit. Care Med.* 1993, 21, 5423; Degre. *Biotherapy* 1996, 8, 219) including tuberculosis (Rook et al. *Med. Malad. Infect.* 1996, 26, 904), *Helicobacter pylori* infection during peptic ulcer disease (Beales et al. *Gastroenterology* 1997, 112, 136), Chaga's disease resulting from *Trypanosoma cruzi* infection (Chandrasekar et al. *Biochem. Biophys. Res. Commun.* 1996, 223, 365), effects of Shiga-like toxin resulting from *E. coli* infection (Harel et al. *J. Clin. Invest.* 1992, 56, 40), the effects of enterotoxin A resulting from *Staphylococcus* infection (Fischer et al. *J. Immunol.* 1990, 144, 4663), meningococcal infection (Waage et al. *Lancet* 1987, 355; Ossege et al. *J. Neurolog. Sci.* 1996, 144, 1), and infections from *Borrelia burgdorferi* (Brandt et al. *Infect. Immunol.* 1990, 58, 983), *Treponema pallidum* (Chamberlin et al. *Infect. Immunol.* 1989, 57, 2872), cytomegalovirus (CMV; Geist et al. *Am. J. Respir. Cell Mol. Biol.* 1997, 16, 31), influenza virus (Beutler et al. *Clin. Res.* 1986, 34, 491 a), Sendai virus (Goldfield et al. *Proc. Natl. Acad. Sci. USA* 1989, 87, 1490), Theiler's encephalomyelitis virus (Sierra et al. *Immunology* 1993, 78, 399), and the human immunodeficiency virus (HIV; Poli. *Proc. Nat'l. Acad. Sci. USA* 1990, 87, 782; Vyakaram et al. *AIDS* 1990, 4, 21; Badley et al. *J. Exp. Med.* 1997, 185, 55).

A number of diseases are thought to be mediated by excess or undesired matrix-destroying metalloprotease (MMP) activity or by an imbalance in the ratio of the MMPs to the tissue inhibitors of metalloproteinases (TIMPs). These include osteoarthritis (Woessner et al. *J. Biol. Chem.* 1984, 259, 3633), rheumatoid arthritis (Mullins et al. *Biochim. Biophys. Acta* 1983, 695, 117; Woolley et al. *Arthritis Rheum.* 1977, 20, 1231; Gravallese et al. *Arthritis Rheum.* 1991, 34, 1076), septic arthritis (Williams et al. *Arthritis Rheum.* 1990, 33, 533), tumor metastasis (Reich et al. *Cancer Res.* 1988, 48, 3307; Matrisian et al. *Proc. Nat'l. Acad. Sci., USA* 1986, 83, 9413), periodontal diseases (Overall et al. *J. Periodontal Res.* 1987, 22, 81), corneal ulceration (Burns et al. *Invest. Opthalmol. Vis. Sci.* 1989, 30, 1569), proteinuria (Baricos et al. *Biochem. J.* 1988, 254, 609), coronary thrombosis from atherosclerotic plaque rupture (Henney et al. *Proc. Nat'l. Acad. Sci., USA* 1991, 88, 8154), aneurysmal aortic disease (Vine et al. *Clin. Sci.* 1991, 81, 233), birth control (Woessner et al. *Steroids* 1989, 54, 491), dystrophobic epidermolysis bullosa (Kronberger et al. *J. Invest. Dermatol.* 1982, 79, 208), degenerative cartilage loss following traumatic joint injury, osteopenias mediated by MMP activity, tempero mandibular joint disease, and demyelating diseases of the nervous system (Chantry et al. *J. Neurochem.* 1988, 50, 688).

Because inhibition of p38 leads to inhibition of TNF production and MMP production, it is believed inhibition of mitogen activated protein (MAP) kinase p38 enzyme can provide an approach to the treatment of the above listed diseases including osteoporosis and inflammatory disorders such as rheumatoid arthritis and COPD (Badger, A. M.; Bradbeer, J. N.; Votta, B.; Lee, J. C.; Adams, J. L.; Griswold, D. E. *J. Pharm. Exper. Ther.* 1996, 279,1453).

Hypoxia appears to be an important stimulus for VEGF production in malignant cells. Activation of p38 MAP kinase is required for VEGF induction by tumor cells in response to hypoxia (Blaschke, F. et al. *Biochem. Biophys. Res. Commun.* 2002, 296, 890-896; Shemirani, B. et al. *Oral Oncology* 2002, 38, 251-257). In addition to its involvement in angiogenesis through regulation of VEGF secretion, p38 MAP kinase promotes malignant cell invasion, and migration of different tumor types through regulation of collagenase activity and urokinase plasminogen activator expression (Laferriere, J. et al. *J. Biol. Chem.* 2001, 276, 33762-33772; Westermarck, J. et al. *Cancer Res.* 2000, 60, 7156-7162; Huang, S. et al. *J. Biol. Chem.* 2000, 275, 12266-12272; Simon, C. et al. *Exp. Cell Res.* 2001, 271, 344-355). Therefore, inhibition of p38 kinase is also expected to impact tumor growth by interfering with signaling cascades associated with both angiogenesis and malignant cell invasion.

Some diarylureas have been described as having activity as serine-threonine kinase and/or as tyrosine kinase inhibitors. The ultility of these diarylureas as an active ingredient in pharmaceutical compositions for the treatment of cancer, angiogenesis disorders, and inflammatory disorders has been demonstated. See Redman et al., *Bioorg. Med. Chem. Lett.* 2001, 11, 9-12; Smith et al., *Bioorg. Med. Chem. Lett.* 2001, 11, 2775-2778; Dumas et al., *Bioorg. Med. Chem. Lett.* 2000, 10, 2047-2050; Dumas et al., *Bioorg. Med. Chem. Lett.* 2000, 10, 2051-2054; Ranges et al., *Book of Abstracts*, $220^{th}$ ACS National Meeting, Washington, D.C., USA, MEDI 149; Dumas et al., *Bioorg. Med. Chem. Lett.* 2002, 12, 1559-1562; Lowinger et al., *Clin. Cancer Res.* 2000, 6(suppl.), 335; Lyons et al., *Endocr.-Relat. Cancer* 2001, 8, 219-225; Riedl et al., *Book of Abstracts*, $92^{nd}$ AACR Meeting, New Orleans, La., USA, abstract 4956; Khire et al., *Book of Abstracts*, $93^{rd}$ AACR Meeting, San Francisco, Calif., USA, abstract 4211; Lowinger et al., *Curr. Pharm. Design* 2002, 8, 99-110; Regan et al., *J. Med. Chem.* 2002, 45, 2994-3008; Pargellis et al., *Nature Struct. Biol.* 2002, 9(4), 268-272; Carter et al., *Book of Abstracts*, $92^{nd}$ AACR Meeting, New Orleans, La., USA, abstract 4954; Vincent et al., *Book of Abstracts*, $38^{th}$ ASCO Meeting, Orlando, Fla., USA, abstract 1900; Hilger et al., *Book of Abstracts*, $38^{th}$ ASCO Meeting, Orlando, Fla., USA, abstract 1916; Moore et al., *Book of Abstracts*, $38^{th}$ ASCO Meeting, Orlando, Fla., USA, abstract 1816; Strumberg et al., *Book of Abstracts*, $38^{th}$ ASCO Meeting, Orlando, Fla., USA, abstract 121; Madwed J B: *Book of Abstracts, Protein Kinases: Novel Target Identification and Validation for Therapeutic Development*, San Diego, Calif., USA, March 2002; Roberts et al., *Book of Abstracts*, $38^{th}$ ASCO Meeting, Orlando, Fla., USA, abstract 473; Tolcher et al., *Book of Abstracts*, $38^{th}$ ASCO Meeting, Orlando, Fla., USA, abstract 334; and Karp et al., *Book of Abstracts*, $38^{th}$ AACR Meeting, San Francisco, Calif., USA, abstract 2753.

Despite the advancements in the art, there remains a need for improved cancer treatments and treatments of inflammatory disorders. BAY 43-9006 and BIRB 796 are two diarylureas of particular interest. BAY 43-9006 (N-(4-chloro-3-(trifluoromethyl)phenyl)-N'-(4-(2-(N-methylcarbamoyl)-4-pyridyloxy)phenyl)urea) has been described in the art as an inhibitor of c-raf kinase, and shows activity in murine tumor xenograft models (Carter et al., *Book of Abstracts*, $92^{nd}$ AACR Meeting, New Orleans, La., USA, abstract 4954). BIRB 796 (1-(5-tert-butyl-2-(4-methyl-phenyl)-2H-pyrazole-3-yl)-3-[4-(2-morpholinylethoxy)naphthalene-1-yl] urea) is a potent, orally available inhibitor of p38 MAP kinase showing activity in a 5-week model of established collagen-induced arthritis in mice (Regan et al., *J. Med. Chem.* 2002, 45, 2994).

DESCRIPTION OF THE INVENTION

The present invention pertains to:
(i) novel compounds and salts thereof, including diastereoisomeric forms,
(ii) pharmaceutical compositions containing such compounds, and
(iii) use of those compounds or compositions for treating diseases, e.g., hyper-proliferative, angiogenesis, and inflammatory disorders, as a sole agent or in combination with other active ingredients, e.g., cytotoxic therapies.

The compounds of formula I, and salts thereof, including diastereoisomeric forms, (both isolated stereoisomers and mixtures of stereoisomers) are collectively referred to herein as the "compounds of the invention". Formula I is as follows:

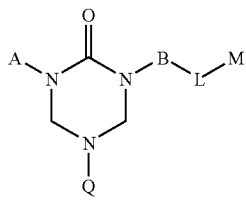

I wherein A and B are 5-10 membered cyclic moieties which are optionally substituted with 1-4 substituents independently selected from the group consisting of $R^1$, $OR^1$, $NR^1R^2$, $S(O)_pR^1$, $SO_2NR^1R^2$, $C(O)NR^1R^2$, $C(NR^1)R^2$, $NR^1SO_2R^2$, $C(O)R^1$, $C(O)OR^1$, $NR^1C(O)R^2$, $NR^1C(O)OR^2$, halogen, cyano, and nitro and A is additionally $C_3$ to $C_6$ linear or branched alkyl such as isopropyl.

A is preferably:
(i) phenyl, optionally substituted with 1-3 substituents independently selected from the group consisting of $R^1$, $OR^1$, $NR^1R^2$, $S(O)_pR^1$, $SO_2NR^1R^2$, $NR^1SO_2R^2$, $C(O)R^1$, $C(O)OR^1$, $C(O)NR^1R^2$, $NR^1C(O)R^2$, $NR^1C(O)OR^2$, halogen, cyano, and nitro;
(ii) naphthyl, optionally substituted with 1-3 substituents independently selected from the group consisting of $R^1$, $OR^1$, $NR^1R^2$, $S(O)_pR^1$, $SO_2NR^1R^2$, $NR^1SO_2R^2$, $C(O)R^1$, $C(O)OR^1$, $C(O)NR^1R^2$, $NR^1C(O)R^2$, $NR^1C(O)OR^2$, halogen, cyano, and nitro;
(iii) 5 and 6 membered monocyclic heteroaryl, having 1-3 heteroatoms independently selected from the group consisting of O, N and S, optionally substituted with 1-3 substituents independently selected from the group consisting of $R^1$, $OR^1$, $NR^1R^2$, $S(O)_pR^1$, $SO_2NR^1R^2$, $NR^1SO_2R^2$, $C(O)R^1$, $C(O)OR^1$, $C(O)NR^1R^2$, $NR^1C(O)R^2$, $NR^1C(O)OR^2$, halogen, cyano, and nitro;
(iv) 8 to 10 membered bicyclic heteroaryl, having 1-6 heteroatoms independently selected from the group consisting of O, N and S, optionally substituted with 1-3 substituents independently selected from the group consisting of $R^1$, $OR^1$, $NR^1R^2$, $S(O)_pR^1$, $SO_2NR^1R^2$, $NR^1SO_2R^2$, $C(O)R^1$, $C(O)OR^1$, $C(O)NR^1R^2$, $NR^1C(O)R^2$, $NR^1C(O)OR^2$, halogen, cyano, and nitro; or (v) a group of the formula

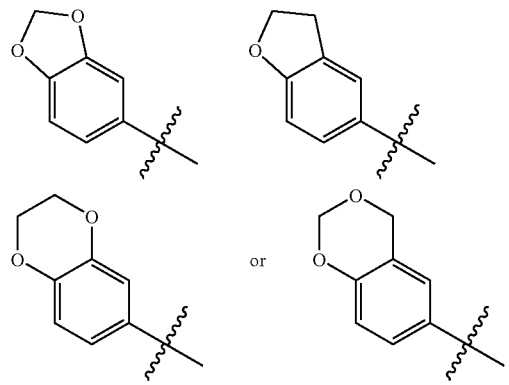

optionally substituted with 1-4 substituents independently selected from the group consisting of $R^1$, $OR^1$, $NR^1R^2$, $S(O)_pR^1$, $SO_2NR^1R^2$, $NR^1SO_2R^2$, $C(O)R^1$, $C(O)OR^1$, $C(O)NR^1R^2$, $NR^1C(O)R^2$, $NR^1C(O)OR^2$, halogen, cyano, and nitro.

B is preferably:
(i) phenyl or naphthyl, optionally substituted with 1-3 substituents independently selected from the group consisting of $C_1$-$C_5$ linear or branched alkyl, $C_1$-$C_5$ linear or branched haloalkyl up to perhalo, $C_1$-$C_3$ alkoxy, $C_1$-$C_3$ haloalkoxy up to per haloalkoxy, hydroxy, amino, $C_1$-$C_3$ alkylamino, $C_1$-$C_6$ dialkylamino, halogen, cyano, and nitro; or
(ii) 5-6 membered monocyclic heteroaryl groups, having 1-4 heteroatoms independently selected from the group consisting of O, N and S, optionally substituted with 1-3 substituents independently selected from the group consisting of $C_1$-$C_5$ linear or branched alkyl, $C_1$-$C_5$ linear or branched haloalkyl up to perhalo, $C_1$-$C_3$ alkoxy, $C_1$-$C_3$ haloalkoxy up to per haloalkoxy, hydroxy, amino, $C_1$-$C_3$ alkylamino, $C_1$-$C_6$ dialkylamino, halogen, cyano, and nitro.

B is most preferably phenyl, naphthyl, or pyridyl, optionally substituted with 1-4 substituents are, independently, $C_1$-$C_5$ linear or branched alkyl, $C_1$-$C_5$ linear or branched haloalkyl, $C_1$-$C_3$ alkoxy, hydroxy, amino, $C_1$-$C_3$ alkylamino, $C_1$-$C_6$ dialkylamino, halogen, cyano, or nitro.

L is a bridging group which is
(a) —$(CH_2)_m$—O—$(CH_2)_l$—,
(b) —$(CH_2)_m$—$(CH_2)_l$—,
(c) —$(CH_2)_m$—C(O)—$(CH_2)_l$—,
(d) —$(CH_2)_m$—$NR^3$—$(CH_2)_l$—,
(e) —$(CH_2)_m$—$NR^3C(O)$—$(CH_2)_l$—,
(f) —$(CH_2)_m$—S—$(CH_2)_l$—,
(g) —$(CH_2)_m$—$C(O)NR^3$—$(CH_2)_l$—,
(h) —$(CH_2)_m$—$CF_2$—$(CH_2)_l$—,
(i) —$(CH_2)_m$—$CCl_2$—$(CH_2)_l$—,
(j) —$(CH_2)_m$—CHF—$(CH_2)_l$—,
(k) —$(CH_2)_m$—CH(OH)—$(CH_2)_l$—;
(l) —$(CH_2)_m$—C≡C—$(CH_2)_l$—; or
(m) —$(CH_2)_m$—C=C—$(CH_2)_l$—;
m and l are integers independently selected from 0-4.
When L is —$(CH_2)_m$—$(CH_2)_l$—, and m and l are 0, then L is a single bond.

M is:
(i) phenyl, optionally substituted with 1-3 substituents independently selected from the group consisting of $R^4$, $OR^4$, $NR^4R^5$, $S(O)_qR^4$, $SO_2NR^4R^5$, $C(O)NR^4R^5$, $C(NR^4)R^5$, $NR^4SO_2R^5$, $C(O)R^4$, $C(O)OR^4$, $NR^4C(O)R^5$, $NR^4C(O)OR^5$, halogen, cyano, and nitro;

(ii) naphthyl, optionally substituted with 1-3 substituents independently selected from the group consisting of $R^4$, $OR^4$, $NR^4R^5$, $S(O)_qR^4$, $SO_2NR^4R^5$, $C(O)NR^4R^5$, $C(NR^4)R^5$, $NR^4SO_2R^5$, $C(O)R^4$, $C(O)OR^4$, $NR^4C(O)R^5$, $NR^4C(O)OR^5$, halogen, cyano, and nitro;

(iii) 5 and 6 membered monocyclic heteroaryl, having 1-3 heteroatoms independently selected from the group consisting of O, N and S, optionally substituted with 1-3 substituents independently selected from the group consisting $R^4$, $OR^4$, $NR^4R^5$, $S(O)_qR^4$, $SO_2NR^4R^5$, $C(O)NR^4R^5$, $C(NR^4)R^5$, $NR^4SO_2R^5$, $C(O)R^4$, $C(O)OR^4$, $NR^4C(O)R^5$, $NR^4C(O)OR^5$, halogen, cyano, nitro and oxides (e.g. =O, —O⁻ or —OH);

(iv) 8 to 10 membered bicyclic heteroaryl, having 1-6 heteroatoms independently selected from the group consisting of O, N and S, optionally substituted with 1-3 substituents independently selected from the group consisting of $R^4$, $OR^4$, $NR^4R^5$, $S(O)_qR^4$, $SO_2NR^4R^5$, $C(O)NR^4R^5$, $C(NR^4)R^5$, $NR^4SO_2R^5$, $C(O)R^4$, $C(O)OR^4$, $NR^4C(O)R^5$, $NR^4C(O)OR^5$, halogen, cyano, nitro and oxides (e.g. =O, —O⁻ or —OH);

(v) saturated and partially saturated $C_3$-$C_7$ monocyclic carbocyclic moiety optionally substituted with 1-3 substituents independently selected from the group consisting of $R^4$, $OR^4$, $NR^4R^5$, $S(O)_qR^4$, $SO_2NR^4R^5$, $C(O)NR^4R^5$, $C(NR^4)R^5$, $C(O)R^4$, $C(O)OR^4$, $NR^4C(O)R^5$, $NR^4C(O)OR^5$, halogen, cyano, and nitro;

(vi) saturated and partially saturated $C_5$-$C_{12}$ bicyclic carbocyclic moiety, optionally substituted with 1-3 substituents independently selected from the group consisting of $R^4$, $OR^4$, $NR^4R^5$, $S(O)_qR^4$, $SO_2NR^4R^5$, $C(O)NR^4R^5$, $C(NR^4)R^5$, $NR^4SO_2R^5$, $C(O)R^4$, $C(O)OR^4$, $NR^4C(O)R^5$, $NR^4C(O)OR^5$, halogen, cyano, and nitro;

(vii) saturated and partially saturated 5 to 7 membered monocyclic heterocyclic moiety, having 1-3 heteroatoms independently selected from the group consisting of O, N and S, optionally substituted with 1-3 substituents independently selected from the group consisting of $R^4$, $OR^4$, $NR^4R^5$, $S(O)_qR^4$, $SO_2NR^4R^5$, $C(O)NR^4R^5$, $C(NR^4)R^5$, $NR^4SO_2R^5$, $C(O)R^4$, $C(O)OR^4$, $NR^4C(O)R^5$, $NR^4C(O)OR^5$, halogen, cyano, nitro and oxides (e.g. =O, —O⁻ or —OH); or (viii) saturated and partially saturated 7 to 12 membered bicyclic heterocyclic moiety, having 1-6 heteroatoms independently selected from the group consisting of O, N and S, optionally substituted with 1-3 substituents independently selected from the group consisting of $R^4$, $OR^4$, $NR^4R^5$, $S(O)_qR^4$, $SO_2NR^4R^5$, $C(O)NR^4R^5$, $C(NR^4)R^5$, $NR^4SO_2R^5$, $C(O)R^4$, $C(O)OR^4$, $NR^4C(O)R^5$, $NR^4C(O)OR^5$, halogen, cyano, nitro and oxides (e.g. =O, —O⁻ or —OH).

M is preferably a nitrogen-containing, monocyclic or bicyclic, saturated, partially saturated or aromatic group, such as preferably pyridine, quinoline, morpholine, indazole, isoquinoline, pyrimidine, and benzimidazole, optionally substituted as above,.

M is most preferably pyridine, optionally substituted as above.

Each $R^1$, $R^2$, $R^3$, $R^4$, $R^5$ and Q is independently selected from the group consisting of:
(a) hydrogen,
(b) $C_1$-$C_5$ linear, branched, or cyclic alkyl,
(c) $C_1$-$C_5$ linear or branched hydroxy alkyl,
(d) $C_1$-$C_5$ linear or branched alkoxy substituted —$C_1$-$C_5$ linear or branched alkyl,
(e) phenyl,
(f) 5-6 membered monocyclic heteroaryl having 1-4 heteroatoms selected from the group consisting of O, N and S or 8-10 membered bicyclic heteroaryl having 1-6 heteroatoms selected from the group consisting of O, N and S,
(g) $C_1$-$C_3$ alkyl-phenyl,
(h) $C_1$-$C_3$ heteroaryl-alkyl having 1-4 heteroatoms selected from the group consisting of O, N and S, wherein said heteroaryl group is a 5-6 membered monocyclic heteroaryl or a 8-10 membered bicyclic heteroaryl, and
(i) up to per-halo substituted $C_1$-$C_5$ linear, branched or cyclic alkyl.

Each $R^1$, $R^2$, $R^3$, $R^4$, $R^5$ and Q, when not hydrogen or perhalo substituted $C_1$-$C_5$ linear or branched alkyl, is optionally substituted with 1-3 substituents independently selected from the group consisting of $C_1$-$C_5$ linear or branched alkyl, up to perhalo substituted $C_1$-$C_5$ linear or branched alkyl, $C_1$-$C_3$ alkoxy, hydroxy, carboxy, amino, $C_1$-$C_3$ alkylamino, $C_1$-$C_6$ dialkylamino, halogen, cyano, and nitro;

The variables p and q are integers independently selected from 0, 1, or 2.

In a group of compounds of interest,

A of formula I is phenyl, optionally substituted with 1-3 substituents independently selected from the group consisting of $R^1$, $OR^1$, $NR^1R^2$, $S(O)_pR^1$, $SO_2NR^1R^2$, $NR^1SO_2R^2$, $C(O)R^1$, $C(O)OR^1$, $C(O)NR^1R^2$, $NR^1C(O)R^2$, $NR^1C(O)OR^2$, halogen, cyano, and nitro;

B is phenyl, optionally substituted with 1-3 substituents independently selected from the group consisting of $C_1$-$C_5$ linear or branched alkyl, $C_1$-$C_5$ linear or branched haloalkyl up to perhalo, $C_1$-$C_3$ alkoxy, $C_1$-$C_3$ haloalkoxy up to per haloalkoxy, hydroxy, amino, $C_1$-$C_3$ alkylamino, $C_1$-$C_6$ dialkylamino, halogen, cyano, and nitro;

L is —O— or —S—,

M is phenyl, pyridine, quinoline, morpholine, indazole, isoquinoline, pyrimidine, or benzimidazole, optionally substituted with 1-3 substituents independently selected from the group consisting of $R^4$, $OR^4$, $NR^4R^5$, $S(O)_qR^4$, $SO_2NR^4R^5$, $C(O)NR^4R^5$, $C(NR^4)R^5$, $NR^4SO_2R^5$, $C(O)R^4$, $C(O)OR^4$, $NR^4C(O)R^5$, $NR^4C(O)OR^5$, halogen, cyano, and nitro;

each $R^1$, $R^2$, $R^4$, $R^5$ and Q is independently selected from the group consisting of:
(a) hydrogen,
(b) $C_1$-$C_5$ linear, branched, or cyclic alkyl,
(c) $C_1$-$C_5$ linear or branched hydroxy alkyl,
(d) $C_1$-$C_5$ linear or branched alkoxy substituted —$C_1$-$C_5$ linear or branched alkyl,
(e) phenyl,
(f) pyridinyl
(g) $C_1$-$C_3$ alkyl-phenyl,
(h) $C_1$-$C_3$ alkyl-pyridinyl or
(i) up to per-halo substituted $C_1$-$C_5$ linear, branched or cyclic alkyl and the variables p and q are integers independently selected from 0, 1, or 2.

Preferably, M is phenyl or pyridine, and more preferably, M is pyridine.

In another group of compounds of interest,

A of formula I is pyridinyl, optionally substituted with 1-3 substituents independently selected from the group consisting of $R^1$, $OR^1$, $NR^1R^2$, $S(O)_pR^1$, $SO_2NR^1R^2$, $NR^1SO_2R^2$, $C(O)R^1$, $C(O)OR^1$, $C(O)NR^1R^2$, $NR^1C(O)R^2$, $NR^1C(O)OR^2$, halogen, cyano, and nitro;

B is phenyl, optionally substituted with 1-3 substituents independently selected from the group consisting of $C_1$-$C_5$ linear or branched alkyl, $C_1$-$C_5$ linear or branched haloalkyl up to perhalo, $C_1$-$C_3$ alkoxy, $C_1$-$C_3$ haloalkoxy up to per haloalkoxy, hydroxy, amino, $C_1$-$C_3$ alkylamino, $C_1$-$C_6$ dialkylamino, halogen, cyano, and nitro;

L is —O— or —S—,

M is phenyl, pyridine, quinoline, morpholine, indazole, isoquinoline, pyrimidine, or benzimidazole, optionally substituted with 1-3 substituents which independently are $R^4$, $OR^4$, $NR^4R^5$, $S(O)_qR^4$, $SO_2NR^4R^5$, $C(O)NR^4R^5$, $C(NR^4)R^5$, $NR^4SO_2R^5$, $C(O)R^4$, $C(O)OR^4$, $NR^4C(O)R^5$, $NR^4C(O)OR^5$, halogen, cyano, or nitro;

each $R^1$, $R^2$, $R^4$, $R^5$ and Q is independently:
(a) hydrogen,
(b) $C_1$-$C_5$ linear, branched, or cyclic alkyl,
(c) $C_1$-$C_5$ linear or branched hydroxy alkyl,
(d) $C_1$-$C_5$ linear or branched alkoxy substituted —$C_1$-$C_5$ linear or branched alkyl,
(e) phenyl,
(f) pyridinyl
(g) $C_1$-$C_3$ alkyl-phenyl,
(h) $C_1$-$C_3$ alkyl-pyridinyl or
(i) up to per-halo substituted $C_1$-$C_5$ linear, branched or cyclic alkyl and the variables p and q are integers independently selected from 0, 1, or 2.

Preferably, M is phenyl or pyridine, and more preferably, M is pyridine.

In another group of compounds of interest,

A of formula I is pyrazole, optionally substituted with 1-3 substituents independently selected from the group consisting of $R^1$, $OR^1$, $NR^1R^2$, $S(O)_pR^1$, $SO_2NR^1R^2$, $NR^1SO_2R^2$, $C(O)R^1$, $C(O)OR^1$, $C(O)NR^1R^2$, $NR^1C(O)R^2$, $NR^1C(O)OR^2$, halogen, cyano, and nitro;

B is phenyl or naphthyl, optionally substituted with 1-3 substituents independently selected from the group consisting of $C_1$-$C_5$ linear or branched alkyl, $C_1$-$C_5$ linear or branched haloalkyl up to perhalo, $C_1$-$C_3$ alkoxy, $C_1$-$C_3$ haloalkoxy up to per haloalkoxy, hydroxy, amino, $C_1$-$C_3$ alkylamino, $C_1$-$C_6$ dialkylamino, halogen, cyano, and nitro;

L is —O— or —S—,

M is phenyl, pyridine, quinoline, morpholine, indazole, isoquinoline, pyrimidine, or benzimidazole, optionally substituted with 1-3 substituents which independently are $R^4$, $OR^4$, $NR^4R^5$, $S(O)_qR^4$, $SO_2NR^4R^5$, $C(O)NR^4R^5$, $C(NR^4)R^5$, $NR^4SO_2R^5$, $C(O)R^4$, $C(O)OR^4$, $NR^4C(O)R^5$, $NR^4C(O)OR^5$, halogen, cyano, or nitro;

each $R^1$, $R^2$, $R^4$, $R^5$ and Q is independently:
(a) hydrogen,
(b) $C_1$-$C_5$ linear, branched, or cyclic alkyl,
(c) $C_1$-$C_5$ linear or branched hydroxy alkyl,
(d) $C_1$-$C_5$ linear or branched alkoxy substituted —$C_1$-$C_5$ linear or branched alkyl,
(e) phenyl,
(f) pyridinyl
(g) $C_1$-$C_3$ alkyl-phenyl,
(h) $C_1$-$C_3$ alkyl-pyridinyl or
(i) up to per-halo substituted $C_1$-$C_5$ linear, branched or cyclic alkyl and the variables p and q are integers independently selected from 0, 1, or 2.

Preferably, M is pyridine or morpholine.

In another group of compounds of formula I of interest,

A is phenyl, optionally substituted with 1-3 substituents independently selected from the group consisting of $R^1$, $OR^1$ and halogen;

B is phenyl, optionally substituted with 1-3 substituents independently selected from the group consisting of $C_1$-$C_5$ linear or branched alkyl, $C_1$-$C_5$ linear or branched haloalkyl up to perhalo, $C_1$-$C_3$ alkoxy, $C_1$-$C_3$ haloalkoxy up to per haloalkoxy, hydroxy, amino, $C_1$-$C_3$ alkylamino, $C_1$-$C_6$ dialkylamino, halogen, cyano, and nitro;

L is —O— or —S—:

M is pyridinyl, optionally with 1-3 substituents independently selected from the group consisting $R^4$, $OR^4$, $NR^4R^5$, $S(O)_qR^4$, $SO_2NR^4R^5$, $C(O)NR^4R^5$, $C(NR^4)R^5$, $NR^4SO_2R^5$, $C(O)R^4$, $C(O)OR^4$, $NR^4C(O)R^5$, $NR^4C(O)OR^5$, halogen, cyano, nitro and oxides;

each $R^4$, $R^5$ and Q is independently:
(a) hydrogen,
(b) $C_1$-$C_5$ linear, branched, or cyclic alkyl,
(c) $C_1$-$C_5$ linear or branched hydroxy alkyl,
(d) $C_1$-$C_5$ linear or branched alkoxy substituted —$C_1$-$C_5$ linear or branched alkyl,
(e) phenyl,
(f) pyridinyl
(g) $C_1$-$C_3$ alkyl-phenyl,
(h) $C_1$-$C_3$ alkyl-pyridinyl or
(i) up to per-halo substituted $C_1$-$C_5$ linear, branched or cyclic alkyl and the variables p and q are integers independently selected from 0, 1, or 2.

In another group of compounds of formula I of interest, A is of the formula X:

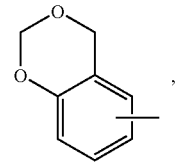

X

A is optionally substituted with 1-4 substituents independently selected from the group consisting of $R^1$, $OR^1$, $NR^1R^2$, $S(O)_pR^1$, $SO_2NR^1R^2$, $NR^1SO_2R^2$, $C(O)R^1$, $C(O)OR^1$, $C(O)NR^1R^2$, $NR^1C(O)R^2$, $NR^1C(O)OR^2$, halogen, cyano, and nitro, B is phenyl, optionally substituted with 1-3 substituents independently selected from the group consisting of $C_1$-$C_5$ linear or branched alkyl, $C_1$-$C_5$ linear or branched haloalkyl up to perhalo, $C_1$-$C_3$ alkoxy, $C_1$-$C_3$ haloalkoxy up to per haloalkoxy, hydroxy, amino, $C_1$-$C_3$ alkylamino, $C_1$-$C_6$ dialkylamino, halogen, cyano, and nitro;

L is —O— or —S—:

M is:
(i) phenyl, optionally substituted with 1-3 substituents independently selected from the group consisting of $R^4$, $OR^4$, $NR^4R^5$, $S(O)_qR^4$, $SO_2NR^4R^5$, $C(O)NR^4R^5$, $C(NR^4)R^5$, $NR^4SO_2R^5$, $C(O)R^4$, $C(O)OR^4$, $NR^4C(O)R^5$, $NR^4C(O)OR^5$, halogen, cyano, and nitro; or
(ii) pyridinyl optionally with 1-3 substituents independently selected from the group consisting $R^4$, $OR^4$, $NR^4R^5$, $S(O)_qR^4$, $SO_2NR^4R^5$, $C(O)NR^4R^5$, $C(NR^4)R^5$, $NR^4SO_2R^5$, $C(O)R^4$, $C(O)OR^4$, $NR^4C(O)R^5$, $NR^4C(O)OR^5$, halogen, cyano, nitro and oxides;

where $R^4$, $R^5$ and Q are independently:
(a) hydrogen,
(b) $C_1$-$C_5$ linear, branched, or cyclic alkyl,
(c) $C_1$-$C_5$ linear or branched hydroxy alkyl,
(d) $C_1$-$C_5$ linear or branched alkoxy substituted —$C_1$-$C_5$ linear or branched alkyl,
(e) phenyl,
(f) pyridinyl
(g) $C_1$-$C_3$ alkyl-phenyl,
(h) $C_1$-$C_3$ alkyl-pyridinyl or
(i) up to per-halo substituted $C_1$-$C_5$ linear, branched or cyclic alkyl and the variables p and q are integers independently selected from 0, 1, or 2.

When any moiety is "substituted", it can have up to the highest number of indicated substituents, and each substituent can be located at any available position on the moiety and can be attached through any available atom on the substituent. "Any available position" means any position on the moiety that is chemically accessible through means known in the art or taught herein and that does not create an unduly unstable molecule. When there are two or more substituents on any moiety, each substituent is defined independently of any other substituent and can, accordingly, be the same or different.

The term "optionally substituted" means that the moiety so modified may be either unsubstituted, or substituted with the identified substituent(s).

It is understood that when M is pyridine, quinoline, or isoquinoline, the term "oxide" includes those structures referred to in the art as 1-oxo-pyridine and 1-hydroxy-pyridine. In contrast, when M is a partially saturated or saturated carbocyclic moiety, the term "oxide" represents a keto group.

Where the plural form of the word compounds, salts, and the like, is used herein, this is taken to mean also a single compound, salt, or the like.

The term $C_1$-$C_5$ alkyl means straight or branched chain alkyl groups having from one to five carbon atoms, which may be linear or branched with single or multiple branching. Such groups include methyl, ethyl, n-propyl, isopropyl, n-butyl, isobutyl, sec-butyl, tert-butyl, and the like.

The term halo$C_1$-$C_5$ alkyl means a saturated hydrocarbon radical having up to five carbon atoms, which is substituted with a least one halogen atom, up to perhalo. The radical may be linear or branched with single or multiple branching. The halo substituent(s) include fluoro, chloro, bromo, or iodo. Fluoro, chloro and bromo are preferred, and fluoro and chloro are more preferred. The halogen substituent(s) can be located on any available carbon. When more than one halogen substituent is present on this moiety, they may be the same or different. Examples of such halogenated alkyl substituents include but are not limited to chloromethyl, dichloromethyl, trichloromethyl, fluoromethyl, difluoromethyl, trifluoromethyl, 2,2,2-trifluoroethyl, and 1,1,2,2-tetrafluoroethyl, and the like.

The term $C_1$-$C_3$ alkoxy means straight or branched chain alkoxy group having from one to three saturated carbon atoms which may be linear or branched with single or multiple branching, and includes such groups as methoxy, ethoxy, n-propoxy, isopropoxy, and the like. It also includes halogenated groups such as 2,2-dichloroethoxy, trifluoromethoxy, and the like.

Halo or halogen means fluoro, chloro, bromo, or iodo. Fluoro, chloro and bromo are preferred, and fluoro and chloro are more preferred.

$C_1$-$C_3$ alkylamino means methylamino, ethylamino, propylamino or isopropylamino.

Examples of $C_1$-$C_6$ dialkylamino group include but are not limited to diethylamino, ethyl-isopropylamino, means methylamino, methyl-isobutylamino, dihexylamino.

Monocyclic heteroaryl means an aromatic monocyclic ring having 5 to 6 ring atoms, at least one of which is a hetero atom selected from N, O and S, the remaining atoms being carbon. When more than one hetero atom is present in the moiety, they are selected independently from the other(s) so that they may be the same or different. Monocyclic heteroaryl rings include, but are not limited to pyrrole, furan, thiophene, imidazole, pyrazole, thiazole, oxazole, isoxazole, isothiazole, triazole, tetrazole, thiadiazole, oxadiazole, pyridine, pyrimidine, pyridazine, pyrazine, and triazine.

Bicyclic heteroaryl means fused bicyclic moieties where one of the rings is chosen from the monocyclic heteroaryl rings described above and the second ring is either benzene or another monocyclic heteroaryl ring described above. When both rings in the bicyclic moiety are heteroaryl rings, they may be the same or different, as long as they are chemically accessible by means known in the art. Bicyclic heteroaryl rings include synthetically accessible 5-5, 5-6, or 6-6 fused bicyclic aromatic structures including, for example but not by way of limitation, benzoxazole (fused phenyl and oxazole), quinoline (fused phenyl and pyridine), imidazopyrimidine (fused imidazole and pyrimidine), and the like.

The term "saturated and partially saturated monocyclic and/or bicyclic carbocyclic moiety" includes, but is not limited to cyclopropyl, cyclobutyl, cyclopentyl, cyclohexyl, decahydronapthalene, cyclopentenyl, cyclohexenyl, cyclohexadienyl, tetrahydronaphthalene and the like.

The term "saturated or partially saturated monocyclic and/or bicyclic heterocyclic moiety" includes, by no way of limitation, tetrahydropyranyl, tetrahydrofuranyl, 1,3-dioxolane, 1,4-dioxanyl, morpholinyl, thiomorpholinyl, piperazinyl, piperidinyl, piperidinonyl, tetrahydropyrimidonyl, pentamethylene sulfide, tetramethylene sulfide dihydropyranyl, dihydrofuranyl, dihydrothienyl, dihydropiperidinyl, dihydropyrimidonyl, and the like.

The term "$C_1$-$C_3$ phenyl-alkyl" includes, by no way of limitation, 3-phenyl-propyl, 2-phenyl-1-methyl-ethyl. Substituted examples include 2-[2-chlorophenyl]ethyl, 3,4-dimethylphenyl-methyl, and the like.

The term "$C_1$-$C_3$ heteroaryl-alkyl" includes, by no way of limitation, 3-imidazole-5-yl-propyl, 2-(2-pyridyl)-1-methyl-ethyl. Substituted examples include 2-[3-chloropyridine-5-yl]ethyl, 3,4-dimethylthiophene-2-yl-methyl, and the like.

The compounds of Formula I may contain one or more asymmetric centers, depending upon the location and nature of the various substituents desired. Asymmetric carbon atoms may be present in the (R) or (S) configuration or (R,S) configuration. In certain instances, asymmetry may also be present due to restricted rotation about a given bond, for example, the central bond adjoining two substituted aromatic rings of the specified compounds. Substituents on a ring may also be present in either cis or trans form. It is intended that all such configurations (including enantiomers and diastereomers), are included within the scope of the present invention. Preferred compounds are those with the absolute configuration of the compound of Formula I which produces the more desirable biological activity. Separated, pure or partially purified isomers or racemic mixtures of the compounds of this invention are also included within the scope of the present invention. The purification of said isomers and the separation of said isomeric mixtures can be accomplished by standard techniques known in the art.

The use of pharmaceutically acceptable salts of the compounds of Formula I are also within the scope of this invention. The term "pharmaceutically acceptable salt" refers to a relatively non-toxic, inorganic or organic acid addition salt of a compound of the present invention. For example, see S. M. Berge, et al. "Pharmaceutical Salts," *J. Pharm. Sci.* 1977, 66, 1-19.

Representative salts of the compounds of this invention include the conventional non-toxic salts and the quaternary ammonium salts which are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, tartrate, thiocyanate, tosylate, and undecanoate.

Base salts include alkali metal salts such as potassium and sodium salts, alkaline earth metal salts such as calcium and magnesium salts, and ammonium salts with organic bases such as dicyclohexylamine and N-methyl-D-glucamine. Additionally, basic nitrogen containing groups may be quaternized with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides, aralkyl halides like benzyl and phenethyl bromides and others.

Certain compounds of this invention can be further modified with labile functional groups that are cleaved after in vivo administration to furnish an active agent and the pharmacologically inactive derivatizing (functional) group. These derivatives can be used, for example, to alter the physicochemical properties of the active agent, to target the active agent to a specific tissue, to alter the pharmacokinetic and pharmacodynamic properties of the active agent, and to reduce undesirable side effects. The esters of appropriate compounds of this invention are well-tolerated, pharmaceutically acceptable esters such as alkyl esters including methyl, ethyl, propyl, isopropyl, butyl, isobutyl or pentyl esters. Additional esters such as phenyl-$C_1$-$C_5$ alkyl may be used, although methyl ester is preferred.

Methods for synthesizing prodrugs are described in the following reviews on the subject, which are incorporated herein by reference for their description of these methods:

Higuchi, T.; Stella, V. eds. *Prodrugs As Novel Drug Delivery Systems*. ACS Symposium Series. American Chemical Society: Washington, D.C. (1975).

Roche, E. B. *Design of Biopharmaceutical Properties through Prodrugs and Analogs*. American Pharmaceutical Association: Washington, D.C. (1977).

Sinkula, A. A.; Yalkowsky, S. H. *J Pharm Sci*. 1975, 64, 181-210.

Stella, V. J.; Charman, W. N. Naringrekar, V. H. *Drugs* 1985, 29, 455-473.

Bundgaard, H., ed. *Design of Prodrugs*. Elsevier: New York (1985).

Stella, V. J.; Himmelstein, K. J. *J. Med. Chem*. 1980, 23, 1275-1282.

Han, H-K; Amidon, G. L. *AAPS Pharmsci* 2000, 2, 1-11.

Denny, W. A. *Eur. J. Med. Chem*. 2001, 36, 577-595.

Wermuth, C. G. in Wermuth, C. G. ed. *The Practice of Medicinal Chemistry* Academic Press: San Diego (1996), 697-715.

Balant, L. P.; Doelker, E. in Wolff, M. E. ed. *Burgers Medicinal Chemistry And Drug Discovery* John Wiley & Sons: New York (1997), 949-982.

General Preparative Methods

The particular process to be utilized in the preparation of the compounds used in this embodiment of the invention depends upon the specific compound desired. Such factors as the selection of the specific substituents play a role in the path to be followed in the preparation of the specific compounds of this invention. Those factors are readily recognized by one of ordinary skill in the art.

The compounds of the invention may be prepared by use of known chemical reactions and procedures. Nevertheless, the following general preparative methods are presented to aid the reader in synthesizing the compounds of the present invention, with more detailed particular examples being presented below in the experimental section describing the working examples.

All variable groups of these methods are as described in the generic description if they are not specifically defined below. When a variable group or substituent with a given symbol is used more than once in a given structure, it is to be understood that each of these groups or substituents may be independently varied within the range of definitions for that symbol. It is recognized that compounds of the invention with each claimed optional functional group cannot be prepared with each of the below-listed methods. Within the scope of each method optional substituents are used which are stable to the reaction conditions, or the functional groups which may participate in the reactions are present in protected form where necessary, and the removal of such protective groups is completed at appropriate stages by methods well known to those skilled in the art.

The compounds of the invention can be made according to conventional chemical methods, and/or as disclosed below, from starting materials which are either commercially available or producible according to routine, conventional chemical methods. General methods for the preparation of the compounds are given below, and the preparation of representative compounds is specifically illustrated in examples.

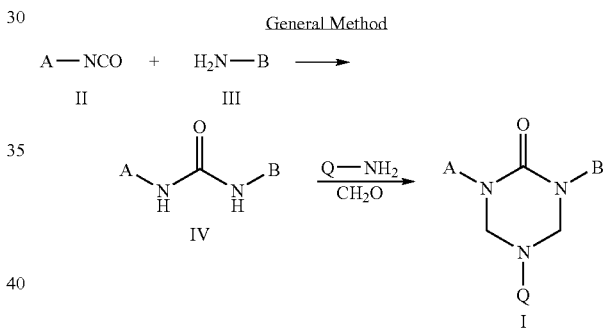

General Method

The compounds (I) can be synthesized according to the reaction sequence shown in the General Method above. Thus, the compounds (IV) can be synthesized by reacting amino compounds (III) with isocyante compounds (II). Reacting the urea compounds (IV) with the amine $H_2NQ$ and formaldehyde furnishes the compounds (I).

The compounds (II) are commercially available or can be synthesized according to methods commonly known to those skilled in the art [e.g. from treatment of an amine with phosgene or a phosgene equivalent such as trichloromethyl chloroformate (diphosgene), bis(trichloromethyl)carbonate (triphosgene), or N,N'-carbonyldiimidazole (CDI); or, alternatively by a Curtius-type rearrangement of an amide, or a carboxylic acid derivative, such as an ester, an acid halide or an anhydride]. The compounds (III) are commercially available or can be synthesized according methods commonly known to those skilled in the art.

In addition, specific preparations of diaryl ureas of Formula (IV) are already described in the patent literature, and can be adapted to the compounds of the present invention. For example, Miller S. et al, "Inhibition of p38 Kinase using Symmetrical and Unsymmetrical Diphenyl Ureas" PCT Int. Appl. WO 99 32463, Miller, S et al. "Inhibition of raf Kinase using Symmetrical and Unsymmetrical Substituted Diphenyl Ureas" PCT Int. Appl., WO 99 32436, Dumas, J. et al., "Inhibition of p38 Kinase Activity using Substituted Heterocyclic Ureas" PCT Int. Appl., WO 99 32111, Dumas, J. et al., "Method for the Treatment of Neoplasm by Inhibition of raf Kinase using N-Heteroaryl-N'-(hetero)arylureas" PCT Int. Appl., WO 99 32106, Dumas, J. et al., "Inhibition of p38 Kinase Activity using Aryl- and Heteroaryl-Substituted Heterocyclic Ureas" PCT Int. Appl., WO 99 32110, Dumas, J., et al., "Inhibition of raf Kinase using Aryl- and Heteroaryl-Substituted Heterocyclic Ureas" PCT Int. Appl., WO 99 32455, Riedl, B., et al., "O-Carboxy Aryl Substituted Diphenyl Ureas as raf Kinase Inhibitors" PCT Int. Appl., WO 00 42012, Riedl, B., et al., "O-Carboxy Aryl Substituted Diphenyl Ureas as p38 Kinase Inhibitors" PCT Int. Appl., WO 00 41698, Dumas, J. et al. "Heteroaryl ureas containing nitrogen hetero-atoms as p38 kinase inhibitors" U.S. Pat. Appl. Publ., US 20020065296, Dumas, J. et al. "Preparation of N-aryl-N'-[(acylphenoxy) phenyl]ureas as raf kinase inhibitors" PCT Int. Appl., WO 02 62763, Dumas, J. et al. "Inhibition of raf kinase using quinolyl, isoquinolyl or pyridyl ureas" PCT Int. Appl, WO 02 85857, Dumas, J. et al. "Preparation of quinolyl, isoquinolyl or pyridyl-ureas as inhibitors of raf kinase for the treatment of tumors and/or cancerous cell growth" U.S. Pat. Appl. Publ., US 20020165394. All the preceding patent applications are hereby incorporated by reference.

A specific preparation of BIRB 796 (1-(5-tert-butyl-2-(4-methyl-phenyl)-2H-pyrazole-3-yl)-3-[4-(2-morpholinylethoxy)naphthalene-1-yl]urea) is described in the literature (Regan et al., *J. Med. Chem.* 2002, 45, 2994; Zhang, L-H, et al., PCT Int. Appl., WO 01 04115).

The reaction of the compounds (II) with (III) is carried out preferably in a solvent. Suitable solvents comprise the customary organic solvents which are inert under the reaction conditions. Non-limiting examples include ethers such as diethyl ether, dioxane, tetrahydrofuran, 1,2-dimethoxy ethane; hydrocarbons such as benzene, toluene, xylene, hexane, cyclohexane, mineral oil fractions; halogenated hydrocarbons such as dichloromethane, trichloromethane, carbon tetrachloride, dichloroethane, trichloroethylene, chlorobenzene; alcohols such as methanol, ethanol, n-propanol, isopropanol; esters such as ethyl acetate; ketones such as acetone; nitriles such as acetonitrile; heteroaromatics such as pyridine; polar solvents such as dimethyl formamide and hexamethyl phosphoric acid tris-amide; and mixtures of the above-mentioned solvents. Toluene, benzene, and dichloromethane are preferred.

The compounds (III) are generally employed in an amount of from 1 to 3 mol per mol of compounds (II); an equimolar amount or slight excess of compounds (III) is preferred.

The reaction of the compounds (II) with (III) is generally carried out within a relatively wide temperature range. In general, they are carried out in a range of from −20 to 200° C., preferably from 0 to 100° C., and more preferably from 25 to 50° C. The steps of this reaction are generally carried out under atmospheric pressure. However, it is also possible to carry them out under superatmospheric pressure or under reduced pressure (for example, in a range of from 0.5 to 5 bar). The reaction time can generally be varied within a relatively wide range. In general, the reaction is finished after a period of from 2 to 24 hours, preferably from 6 to 12 hours.

The amines $QNH_2$ are commercially available or can be synthesized according methods commonly known to those skilled in the art.

The reaction of the compounds (IV) with the amines $QNH_2$ and formaldehyde is described in Knapp, S.; Hale, J. J.; Bastos, M.; Gibson, F. S. Tetrahedron Lett. 1990, 31, 2109-2112; Knapp, S.; Hale, J. J.; Bastos, M.; Molina, A.; Chen K. Y. J. Org. Chem. 1992, 57, 6239-6256. Kovalenko, A. L.; Serov, Yu. V.; Tselinskii, I. V.; Nikonov, A. A *Zhurnal Organicheskoi Khimii*, 1991, 27, 2388-2391. Nevertheless, the following general preparative method is presented to aid the reader in synthesizing the compounds of the present invention.

The reaction of the compounds (IV) with the amines $QNH_2$ and formaldehyde is carried out preferably in a solvent. Suitable solvents comprise water and the customary organic solvents which are inert under the reaction conditions. Non-limiting examples include ethers such as diethyl ether, dioxane, tetrahydrofuran, 1,2-dimethoxy ethane; hydrocarbons such as benzene, toluene, xylene, hexane, cyclohexane, mineral oil fractions; halogenated hydrocarbons such as dichloromethane, trichloromethane, carbon tetrachloride, dichloroethane, trichloro-ethylene, chlorobenzene; alcohols such as methanol, ethanol, n-propanol, isopropanol; esters such as ethyl acetate; ketones such as acetone; nitriles such as acetonitrile; heteroaromatics such as pyridine; polar solvents such as dimethyl formamide and hexamethyl phosphoric acid tris-amide; and mixtures of the above-mentioned solvents. Water, and a mixture of water and toluene are preferred.

The amines $QNH_2$ are generally employed in an amount of from 1 to 5 mol per mol of compounds (IV); a 2 mol excess of compounds (IV) is preferred.

The reaction of the compounds (IV) with the amines $QNH_2$ and formaldehyde is generally carried out within a relatively wide temperature range. In general, they are carried out in a range of from −20 to 200° C., preferably from 0 to 120° C., and more preferably from 50 to 120° C. The steps of this reaction are generally carried out under atmospheric pressure. However, it is also possible to carry them out under superatmospheric pressure or under reduced pressure (for example, in a range of from 0.5 to 5 bar). The reaction time can generally be varied within a relatively wide range. In general, the reaction is finished after a period of from 2 to 24 hours, preferably from 6 to 12 hours.

Synthetic transformations that may be employed in the synthesis of compounds of Formula I and in the synthesis of intermediates involved in the synthesis of compounds of Formula I are known by or accessible to one skilled in the art. Collections of synthetic transformations may be found in compilations, such as:

J. March. *Advanced Organic Chemistry*, 4th ed.; John Wiley: New York (1992)

R. C. Larock. *Comprehensive Organic Transformations*, 2nd ed.; Wiley-VCH: New York (1999)

F. A. Carey; R. J. Sundberg. *Advanced Organic Chemistry*, 2nd ed.; Plenum Press: New York (1984)

T. W. Greene; P. G. M. Wuts. *Protective Groups in Organic Synthesis*, 3rd ed.; John Wiley: New York (1999)

L. S. Hegedus. *Transition Metals in the Synthesis of Complex Organic Molecules*, 2nd ed.; University Science Books: Mill Valley, Calif. (1994)

L. A. Paquette, Ed. *The Encyclopedia of Reagents for Organic Synthesis*; John Wiley: New York (1994)

A. R. Katritzky; O. Meth-Cohn; C. W. Rees, Eds. *Comprehensive Organic Functional Group Transformations*; Pergamon Press: Oxford, UK (1995)

G. Wilkinson; F. G A. Stone; E. W. Abel, Eds. *Comprehensive Organometallic Chemistry*; Pergamon Press: Oxford, UK (1982)

B. M. Trost; I. Fleming. *Comprehensive Organic Synthesis*; Pergamon Press: Oxford, UK (1991)

A. R. Katritzky; C. W. Rees Eds. *Comprehensive Heterocylic Chemistry*; Pergamon Press: Oxford, UK (1984)

A. R. Katritzky; C. W. Rees; E. F. V. Scriven, Eds. *Comprehensive Heterocylic Chemistry II*; Pergamon Press: Oxford, UK (1996)

C. Hansch; P. G. Sammes; J. B. Taylor, Eds. *Comprehensive Medicinal Chemistry*: Pergamon Press: Oxford, UK (1990).

In addition, recurring reviews of synthetic methodology and related topics include *Organic Reactions*; John Wiley: New York; *Organic Syntheses*; John Wiley: New York; *Reagents for Organic Synthesis*: John Wiley: New York; *The Total Synthesis of Natural Products*; John Wiley: New York; *The Organic Chemistry of Drug Synthesis*; John Wiley: New York; *Annual Reports in Organic Synthesis*; Academic Press: San Diego Calif.; and *Methoden der Organischen Chemie* (Houben-Weyl); Thieme: Stuttgart, Germany. Furthermore, databases of synthetic transformations include *Chemical Abstracts*, which may be searched using either CAS OnLine or SciFinder, *Handbuch der Organischen Chemie*(Beilstein), which may be searched using SpotFire, and REACCS.

Compositions of the Compounds of this Invention

This invention also relates to pharmaceutical compositions containing one or more compounds of the present invention. These compositions can be utilized to achieve the desired pharmacological effect by administration to a patient in need thereof. A patient, for the purpose of this invention, is a mammal, including a human, in need of treatment for the particular condition or disease. Therefore, the present invention includes pharmaceutical compositions which are comprised of a pharmaceutically acceptable carrier and a pharmaceutically effective amount of a compound, or salt thereof, of the present invention. A pharmaceutically acceptable carrier is any carrier which is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is that amount which produces a result or exerts an influence on the particular condition being treated. The compounds of the present invention can be administered with pharmaceutically-acceptable carriers well known in the art using any effective conventional dosage unit forms, including immediate, slow and timed release preparations, orally, parenterally, topically, nasally, ophthalmically, otically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule which can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatin, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, coloring agents, and flavoring agents such as peppermint, oil of wintergreen, or cherry flavoring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavoring and coloring agents.

The compounds of this invention may also be administered parenterally, that is, subcutaneously, intravenously, intraocularly, intrasynovially, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulation ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such material are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations which are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al, "Compendium of Excipients for Parenteral Formulations" *PDA Journal of Pharmaceutical Science & Technology* 1998, 52(5), 238-311; Strickley, R. G "Parenteral Formulations of Small Molecule Therapeutics Marketed in the United States (1999)-Part-1" *PDA Journal of Pharmaceutical Science & Technology* 1999, 53(6), 324-349; and Nema, S. et al, "Excipients and Their Use in Injectable Products" *PDA Journal of Pharmaceutical Science & Technology* 1997, 51(4), 166-171.

Commonly used pharmaceutical ingredients which can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC-CClF_2$ and $CClF_3$)

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colorants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate)

flavorants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

table/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

It is believed that one skilled in the art, utilizing the preceding information, can utilize the present invention to its fullest extent. Nevertheless, the following are examples of pharmaceutical formulations that can be used in the method of the present invention. They are for illustrative purposes only, and are not to be construed as limiting the invention in any way.

Pharmaceutical compositions according to the present invention can be illustrated as follows:

Sterile IV Solution: A 5 mg/mL solution of the desired compound of this invention is made using sterile, injectable water, and the pH is adjusted if necessary. The solution is diluted for administration to 1-2 mg/mL with sterile 5% dextrose and is administered as an IV infusion over 60 minutes.

Lyophilized powder for IV administration: A sterile preparation can be prepared with (i) 100-1000 mg of the desired compound of this invention as a lypholized powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular suspension: The following solution or suspension can be prepared, for intramuscular injection:
  50 mg/mL of the desired, water-insoluble compound of this invention
  5 mg/mL sodium carboxymethylcellulose
  4 mg/mL TWEEN 80
  9 mg/mL sodium chloride
  9 mg/mL benzyl alcohol Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit was 100 mg of active ingredient, 0.2 mg of colloidal silicon dioxide, 5 mg of magnesium stearate, 275 mg of microcrystalline cellulose, 11 mg of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Method of Treating Hyper-proliferative Disorders

The present invention relates to a method for using the compounds described above (Compounds of Formula I), including salts and esters thereof and compositions thereof, to treat mammalian hyper-proliferative disorders. This method comprises administering to a mammal in need thereof, including a human, an amount of a compound of this invention, or a pharmaceutically acceptable salt or ester thereof, which is effective to treat the disorder. Hyper-proliferative disorders include but are not limited to solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, and urethral cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal/hypopharyngeal/nasopharyngeal/oropharyngeal cancer, and lip and oral cavity cancer.

Lymphomas include, but are not limited to AIDS-related lymphoma, non-Hodgkin's lymphoma, cutaneous T-cell lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The compounds of this invention can be administered as the sole pharmaceutical agent or in combination with one or more other pharmaceutical agents where the combination causes no unacceptable adverse effects. For example, the compounds of this invention can be combined with known anti-hyper-proliferative or other indication agents, and the like, as well as with admixtures and combinations thereof.

Optional anti-hyper-proliferative agents which can be added to the composition include but are not limited to compounds listed on the cancer chemotherapy drug regimens in the 11th Edition of the *Merck Index*, (1996), which is hereby incorporated by reference, such as asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other anti-hyper-proliferative agents suitable for use with the composition of the invention include but are not limited to those compounds acknowledged to be used in the treatment of neoplastic diseases in *Goodman and Gilman's The Pharmacological Basis of Therapeutics* (Ninth Edition), editor Molinoff et al., publ. by McGraw-Hill, pages 1225-1287, (1996), which is hereby incorporated by reference, such as aminoglutethimide, L-asparaginase, azathioprine, 5-azacytidine cladribine, busulfan, diethylstilbestrol, 2',2'-difluorodeoxycytidine, docetaxel, erythrohydroxynonyladenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine.

Other anti-hyper-proliferative agents suitable for use with the composition of the invention include but are not limited to other anti-cancer agents such as epothilone and its derivatives, irinotecan, raloxifen and topotecan.

Generally, the use of cytotoxic and/or cytostatic agents in combination with a compound or composition of the present invention will serve to:

(1) yield better efficacy in reducing the growth of a tumor or even eliminate the tumor as compared to administration of either agent alone, (2) provide for the administration of lesser amounts of the administered chemotherapeutic agents, (3) provide for a chemotherapeutic treatment that is well tolerated in the patient with fewer deleterious pharmacological complications than observed with single agent chemotherapies and certain other combined therapies, (4) provide for treating a broader spectrum of different cancer types in mammals, especially humans, (5) provide for a higher response rate among treated patients, (6) provide for a longer survival time among treated patients compared to standard chemotherapy treatments, (7) provide a longer time for tumor progression, and/or (8) yield efficacy and tolerability results at least as good as those of the agents used alone, compared to known instances where other cancer agent combinations produce antagonistic effects.

Method of Treating Inflammatory Disorders

Clinical studies have linked abnormal tumor necrosis factor (TNF) production and/or signaling to a number of inflammatory and immunomodulatory diseases. These diseases include, but are not limited to rheumatoid arthritis, psoriasis, acute rheumatic fever, sepsis, septic shock, endotoxic shock, toxic shock syndrome, systemic inflammatory response syndrome, inflammatory bowel diseases including Crohn's disease, ulcerative colitis, Jarisch-Herxheimer reactions, asthma, adult respiratory distress syndrome, acute pulmonary fibrotic diseases, and chronic obstructive pulmonary disease.

A number of diseases are thought to be mediated by excess or undesired matrix-destroying metalloprotease (MMP) activity or by an imbalance in the ratio of the MMPs to the tissue inhibitors of metalloproteinases (TIMPs). These include, but are not limited to osteoarthritis, rheumatoid arthritis, septic arthritis, degenerative cartilage loss following traumatic joint injury, osteopenias mediated by MMP activity, and tempero mandibular joint disease.

Because inhibition of p38 leads to inhibition of TNF production and MMP production, inhibition of mitogen activated protein (MAP) kinase p38 enzyme provides an approach to the treatment of the above listed inflammatory diseases.

Release of the Active Principle

Upon dosing in a mammal, the compounds of the present invention undergo a biotransformation. This transformation is either catalyzed by an enzyme of the Is subject treated, or by in vivo hydrolysis, which takes place, for example, in the acidic medium of the stomach after oral administration. As a result, a diaryl urea of formula A—NH—CO—NH—B, which carries potent biological activity as described in the art, is formed upon dosing a mammal with a compound of Formula I. Therefore, compounds of Formula I are useful for the treatment of diseases such as raf-mediated, angiogenesis-mediated, and p38-mediated diseases. Dosing a compound of Formula I instead of the corresponding urea of Formula A—NH—CO—NH—B may carry one or more of the following advantages:

(1) the compound of Formula I may modify overall aqueous solubility, when compared to ureas of formula A—NH CO—NH—B, and bring more desirable physicochemical properties, (2) the safety and tolerability of the drug may be improved when compared to ureas of formula A—NH CO—NH—B, (3) the stability of the compounds of Formula I could be modulated to produce the optimal delivery of the urea of formula A—NH—CO—NH—B to the subject.

Dosage of the Compounds of the Present Invention

Based upon standard laboratory techniques known to evaluate compounds useful for the treatment of hyper-proliferative, angiogenesis, and inflammatory disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200mg/kg bodyweight per day, and preferably from about 0.01 mg/kg to about 20 mg/kg body weight per day. It should be noted that the choice of dosing schedules is particularly important to maximize the efficacy and safety of drugs for the treatment of proliferative disorders, and inflammatory disorders. Clinically useful dosing schedules will range from three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

It is believed that one skilled in the art, using the preceding information and information available in the art, can utilize the present invention to its fullest extent.

It should be apparent to one of ordinary skill in the art that changes and modifications can be made to this invention without departing from the spirit or scope of the invention as it is set forth herein.

EXAMPLES

Abbreviations used in this specification

| | |
|---|---|
| ™ Cremophor | non-ionic emulsifier from BASF, Germany ® |
| DBU | 1,8-diazabicyclo[5.4.0]undec-7-ene |
| DMF | N,N-dimethyl formamide |
| DMSO | dimethyl sulphoxide |
| HPLC | high pressure liquid chromatography |
| LC-MS | liquid chromatography - coupled mass spectroscopy |
| LC RT | liquid chromatography retention time |
| MP | melting point |
| NMR | nuclear resonance spectroscopy |
| TLC | thin layer chromatography |

The yield percentages of the following examples refer to the starting component which was used in the lowest molar amount.

MS method used in the Examples (HPLC/MS):

| | | | | |
|---|---|---|---|---|
| MS equipment: | Micromass Quattro LCZ | | | |
| | ionisation mode: ESI positive/negative | | | |
| HPLC equipment: | HP 1100 | | | |
| | UV detection: 208-400 nm | | | |
| | temperature: 40° C. | | | |
| Column: | ™ Symmetry C 18 | | | |
| | 50 mm × 2.1 mm 3.5 µm | | | |
| Supplier: | Waters | | | |
| Gradient: | Time | | | Flow |
| | [min.] | A: % | B: % | [mL/min.] |
| | 0.00 | 90.0 | 10.0 | 0.50 |
| | 4.00 | 10.0 | 90.0 | 0.50 |
| | 6.00 | 10.0 | 90.0 | 0.50 |

A: 0.05% strength solution of formic acid in water
B: 0.05% strength formic acid in acetonitrile Example 1

1-(4-chloro-3(trifluoromethyl)phenyl)-3-(4-(2-(N-methylcarbamoyl)-4-pyridyloxy)phenyl)-2-oxo-(1,3,5-perhydrotriazapine)

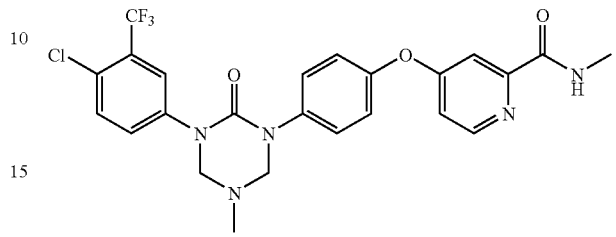

A mixture of methylamine hydrochloride (79.9 mg, 1.18 mmol) and 37% aqueous formaldehyde (3.25 mL, 40.3 mmol) was neutralized with N,N-diisopropylethylamine and stirred for 10 min. N-(4-chloro-3(trifluoromethyl)phenyl)-N'-(4-(2-(N-methylcarbamoyl)-4-pyridyloxy)phenyl)urea (Intermediate 1, preparation described in WO0042012, 250 mg, 0.54 mmol) and toluene (3 mL) were added and the reaction was heated at reflux for 16 hr. The reaction was allowed to cool to room temperature and was extracted with EtOAc (3×10 mL). The combined organic extracts were dried (MgSO4) and concentrated. The crude product was purified by preparative HPLC, which afforded 30 mg (0.0583 mmol, 11%) of Example 1 as a white solid. MP: 82-85 °C; $^1$H-NMR (CD$_3$OD) δ 2.89 (s, 3H), 2.94 (s, 3H), 4.77 (s, 2H), 4.81 (s, 2H), 7.05-7.09 (m, 1H), 7.20 (d, J=8.6, 2H), 7.46 (d, J=9.2, 2H), 7.54-7.65(m, 3H), 7.80 (d, J=2.3, 1H) 8.46 (d, J 6.5, 1H); MS (HPLC/ES) m/z=520.08 (M+1).

Example 2

4-{4-[3-(4-Chloro-3-trifluoromethyl-phenyl)-5-(2-methoxy-ethyl)-2-oxo-[1,3,5]triazinan-1-yl]-3-fluoro-phenoxy}-pyridine-2-carboxylic acid methylamide

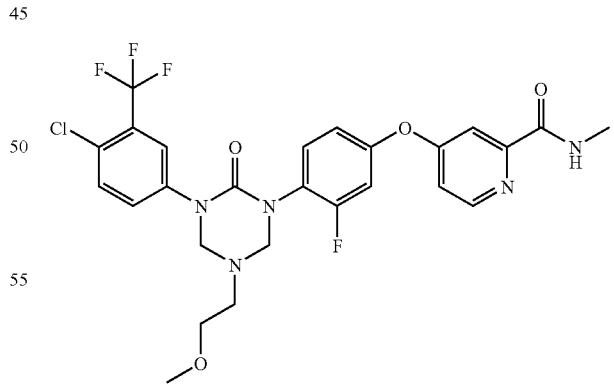

A mixture of methoxyethylamine (46.7 mg, 0.62 mmol), 4-{4-[3-(4-chloro-3-trifluoromethyl-phenyl)-ureido]-3-fluoro-phenoxy}-pyridine-2-carboxylic acid methylamide (300 mg, 0.62 mmol) and 0.8 mL 37% aqueous formaldehyde were stirred at 40° C. for 10-15 min in a 50-mL flask equipped with a Dean-Stark trap. Diisopropylethylamine (120 mg, 0.93 mmol) and toluene (10 mL) were added, and the temperature was raised to 107° C. During a 90-minute period, additional toluene (15 mL) was added to the reaction mixture, and approximately 10 mL distillate was collected. The reaction was cooled and concentrated to afford a solid residue. Chromatography on silica gel using 3:2 ethyl acetate/hexane as the eluant afforded 92.4 mg (yield 25.6%) of Example 2 as a white solid. 1H NMR (400 MHz, DMSO) δ 8.80 (bs, 1H), 8.50 (d, 1H), 7.80 (s, 1H), 7.70 (d, 1H), 7.65 (d, 1H), 7.55 (d, 1H), 7.50 (d, 1H), 7.40 (d, 1H), 7.20 (d, 1H), 7.10 (d, 1H), 4.85 (s, 2H), 4.70 (s, 2H), 3.50 (t, 2H), 3.25 (s, 3H), 3.20 (t, 2H), 2.80 (s, 3H); MS (HPLC/ES) m/z 582.1 (MH+).

Example 3

4-{4-[3-(4-Chloro-3-trifluoromethyl-phenyl)-5-(2-hydroxy-ethyl)-2-oxo-[1,3,5]triazinan-1-yl]-3-fluoro-phenoxy}-pyridine-2-carboxylic acid methylamide

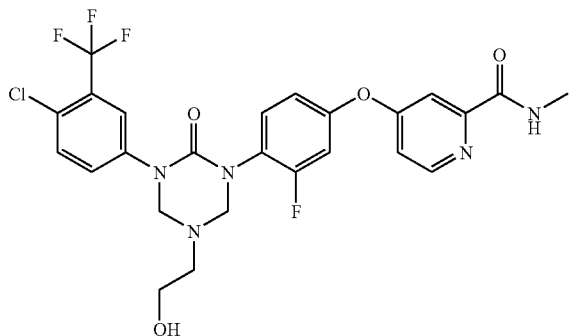

The compound of Example 3 (10 mg, yield 6%) was prepared by using the same method as Example 2. MS (HPLC/ES) m/z 568.1 (MH+), RT=2.85 min.

Example 4

4-{4-[3-(4-Chloro-3-trifluoromethyl-phenyl)-5-(3-hydroxy-propyl)-2-oxo-[1,3,5]triazinan-1-yl]-3-fluoro-phenoxy}-pyridine-2-carboxylic acid methylamide

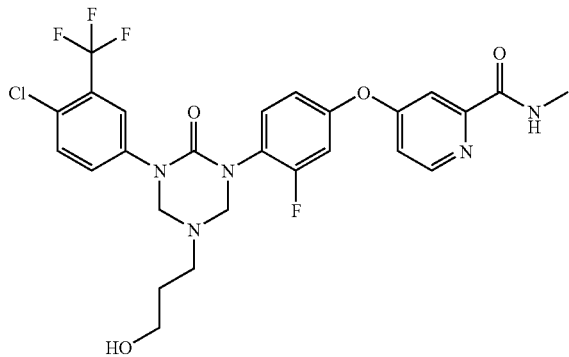

The compound of Example 4 (16.3 mg, yield 4.5%) was also prepared by the same method as described in Example 2. MS (HPLC/ES) m/z 582.6 (MH+), RT=2.82 min.

Example 5

4-{3-Fluoro-4-[5-methyl-2-oxo-3-(2,2,4,4-tetrafluoro-4H-benzo[1,3]dioxin-6-yl)-[1,3,5]triazinan-1-yl]-phenoxy}-pyridine-2-carbonitrile

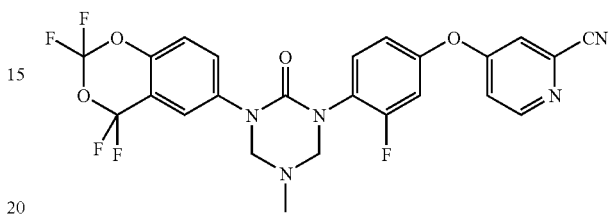

Methylamine hydrochloride (77.63 mg, 1.15 mmol) was weighed into a flask and 37% formaldehyde (3.25 mL, 43.37 mmol) was added. The solution was then neutralized with diisopropylethylamine. A solution of N-(6-(2,2,4,4-tetrafluoro-4H-benzo[1,3]dioxinyl))-N'-(4-(2-cyano-4-pyridyloxy)phenyl)urea (250 mg, 0.52 mmol) in toluene (3 mL) in a separate flask and added to the reaction vessel. The mixture was heated to reflux for 18 hrs, at which point the incomplete reaction was extracted with EtOAc. The organic fractions were combined, dried with sodium sulfate and concentrated in vacuo. The resulting oil was purified via flash chromatography (40:60 to 60:40, EtOAc:Hexanes) to yield 31.3 mg (11.23%) of the purified product. MS: M+H: 534.0. TLC: RF=0.17 (50% EtOAc in hexanes).

Example 6

4-{3-Fluoro-4-[5-methyl-2-oxo-3-(2,2,4,4-tetrafluoro-4H-benzo[1,3]dioxin -6-yl)-[1,3,5]triazinan-1-yl]-phenoxy}-pyridine-2-carboxylic acid methylamide

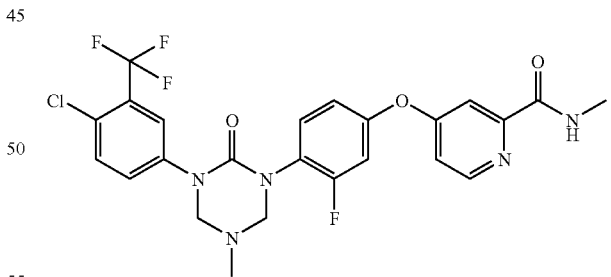

The title compound was synthesized using the same procedure as example 5 above, using 4-{4-[3-(4-chloro-3-trifluoromethyl-phenyl)-ureido]-3-fluoro-phenoxy}-pyridine-2-carboxylic acid methylamide as starting material. Yield: 14.36%, MS: M+H=538.1. TLC: RF=0.39 (100% EtOAc).

Biological Tests

Pharmacokinetics in the Mouse

Female ICr mice received single doses of Example 1 by oral gavage at 30 mg/kg body weight. The vehicle used for administration consisted of 12.5% Cremophor, 12.5% ethanol and 75% saline. Blood samples were collected by cardiac puncture under anesthesia and plasma was isolated by centrifugation. Three animals were used for each time point of 0.5, 1 and 5 hours post dosing. Plasma levels of Example 1 and Intermediate 1 were measured by LC-MS.

Calibration samples (1 to 5,000 ng/mL) were prepared by spiking drug-free mouse plasma with known concentrations of Example 1 and Intermediate 1 and then processed with the study samples. An internal standard (close analog) was spiked at a final concentration of 100 ng/ml. Plasma samples were extracted via protein precipitation using acetonitrile (3:1). After vortexing for 1 minute, samples were centrifuged at 2500 rpm for 15 minutes. Supernatant was transferred to 96-well microtiter plates for LC-MS analysis. Analytes (Example 1 and Intermediate 1) and the internal standard were monitored using MRM transitions consisting of their protonated molecular ions to prominent fragment ions (Example 1 m/z 520 to m/z 270; Intermediate 1 m/z 465 to 252; internal standard m/z 469 to m/z 256). The calibration curve was constructed using least squares linear regression and utilized peak area ratios of the analyte and internal standard. Pharmacokinetic analysis of the measured plasma concentrations was conducted using the Watson® Drug Metabolism Laboratory Information Management System (Innaphase Corp, Philadelphia, Pa.). The results of the experiment indicate that:
(i) the prodrug from Example 1 is very well absorbed in mice.
(ii) significant levels of Intermediate 1 (BAY 43-9006) were detected in plasma after oral administration of the pro-drug Example 1 to mice.

By changing the nature of substituent Q in Formula (I), it is possible to impact the stability, i.e., the speed of hydrolysis) of the prodrug, and therefore to modulate the plasma exposure to the pharmacologically active compound. High stabilities will lead to extended release of the drug, while low stabilities will contribute to high Cmax and short duration of action.

Table 1 contains a summary of the plasma concentrations and pharmacokinetic parameters.

|  | Time (Hours) | Example 1 | Intermediate 1 |
|---|---|---|---|
| Mean Plasma concentration (µM) | 0.5 | 12.1 | 0.1 |
|  | 1 | 13.0 | 0.2 |
|  | 5 | 9.4 | 0.5 |
| AUC (µM · hr) | — | 53.1 | 1.0 |
| Cmax (µM) | — | 13.0 | 0.3 |

What is claimed is:
1. A compound of formula I,

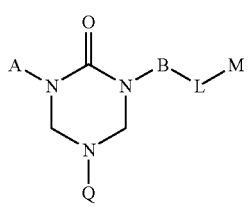

I or a pharmaceutically acceptable salt thereof,
wherein A is
(i) phenyl, optionally substituted with 1-3 substituents independently selected from the group consisting of $R^1$, $OR^1$, $NR^1R^2$, $S(O)_pR^1$, $SO_2NR^1R^2$, $NR^1SO_2R^2$, $C(O)R^1$, $C(O)OR^1$, $C(O)NR^1R^2$, $NR^1C(O)R^2$, $NR^1C(O)OR^2$, halogen, cyano, and nitro;
(ii) naphthyl, optionally substituted with 1-3 substituents independently selected from the group consisting of $R^1$, $OR^1$, $NR^1R^2$, $S(O)_pR^1$, $SO_2NR^1R^2$, $NR^1SO_2R^2$, $C(O)R^1$, $C(O)OR^1$, $C(O)NR^1R^2$, $NR^1C(O)R^2$, $NR^1C(O)OR^2$, halogen, cyano, and nitro;
(iii) 5 and 6 membered monocyclic heteroaryl, having 1-3 heteroatoms independently selected from the group consisting of O, N and S, optionally substituted with 1-3 substituents independently selected from the group consisting of $R^1$, $OR^1$, $NR^1R^2$, $S(O)_pR^1$, $SO_2NR^1R^2$, $NR^1SO_2R^2$, $C(O)R^1$, $C(O)OR^1$, $C(O)NR^1R^2$, $NR^1C(O)R^2$, $NR^1C(O)OR^2$, halogen, cyano, and nitro;
(iv) 8 to 10 membered bicyclic heteroaryl, having 1-6 heteroatoms independently selected from the group consisting of O, N and S, optionally substituted with 1-3 substituents independently selected from the group consisting of $R^1$, $OR^1$, $NR^1R^2$, $S(O)_pR^1$, $SO_2NR^1R^2$, $NR^1SO_2R^2$, $C(O)R^1$, $C(O)OR^1$, $C(O)NR^1R^2$, $NR^1C(O)R^2$, $NR^1C(O)OR^2$, halogen, cyano, and nitro; or
(v) a group of the formula

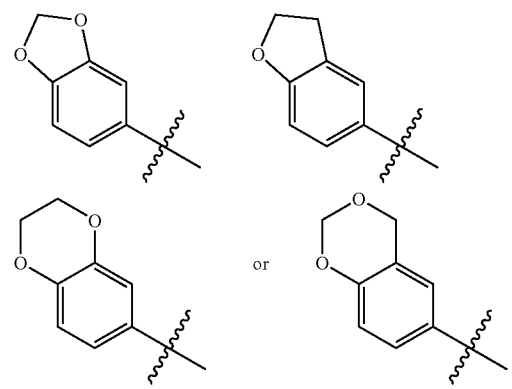

optionally substituted with 1-4 substituents independently selected from the group consisting of $R^1$, $OR^1$, $NR^1R^2$, $S(O)_pR^1$, $SO_2NR^1R^2$, $NR^1SO_2R^2$, $C(O)R^1$, $C(O)OR^1$, $C(O)NR^1R^2$, $NR^1C(O)R^2$, $NR^1C(O)OR^2$, halogen, cyano, and nitro B is (i) phenyl or naphthyl, optionally substituted with 1-3 substituents independently selected from the group consisting of $C_1$-$C_5$ linear or branched alkyl, $C_1$-$C_5$ linear or branched haloalkyl up to perhalo, $C_1$-$C_3$ alkoxy, $C_1$-$C_3$ haloalkoxy up to per haloalkoxy, hydroxy, amino, $C_1$-$C_3$ alkylamino, $C_1$-$C_6$ dialkylamino, cyano, and nitro; and
A is additionally $C_3$ to $C_6$ linear or branched alkyl;
L is a bridging group selected from the group consisting of:
(a) —$(CH_2)_m$—O—$(CH_2)_l$—,
(c) —$(CH_2)_m$—C(O)—$(CH_2)_l$—,
(d) —$(CH_2)_m$—$NR^3$—$(CH_2)_l$—,
(e) —$(CH_2)_m$—$NR^3C(O)$—$(CH_2)_l$—,
(f) —$(CH_2)_m$—S—$(CH_2)_l$—,
(g) —$(CH_2)_m$—$C(O)NR^3$—$(CH_2)_l$—,
(h) —$(CH_2)_m$—$CF_2$—$(CH_2)_l$—,
(i) —$(CH_2)_m$—$CCl_2$—$(CH_2)_l$—,
(j) —$(CH_2)_m$—CHF—$(CH_2)_l$—, and
(k) —$(CH_2)_m$—CH(OH)—$(CH_2)_l$—;
wherein m and l are integers independently selected from 0-4, M is
(i) phenyl, optionally substituted with 1-3 substituents independently selected from the group consisting of $R^4$, $OR^4$, $NR^4R^5$, $S(O)_qR^4$, $SO_2NR^4R^5$, $C(O)NR^4R^5$, $C(NR^4)R^5$, $NR^4SO_2R^5$, $C(O)R^4$, $C(O)OR^4$, $NR^4C(O)R^5$, $NR^4C(O)OR^5$, halogen, cyano, and nitro;
(ii) naphthyl, optionally substituted with 1-3 substituents independently selected from the group consisting of $R^4$, $OR^4$, $NR^4R^5$, $S(O)_qR^4$, $SO_2NR^4R^5$, $C(O)NR^4R^5$, $C(NR^4)R^5$, $NR^4SO_2R^5$, $C(O)R^4$, $C(O)OR^4$, $NR^4C(O)R^5$, $NR^4C(O)OR^5$, halogen, cyano, and nitro;
(iii) 5 and 6 membered monocyclic heteroaryl, having 1-3 heteroatoms independently selected from the group consisting of O, N and S, optionally substituted with 1-3 substituents independently selected from the group consisting $R^4$, $OR^4$, $NR^4R^5$, $S(O)_qR^4$, $SO_2NR^4R^5$, $C(O)NR^4R^5$, $C(NR^4)R^5$, $NR^4SO_2R^5$, $C(O)R^4$, $C(O)OR^4$, $NR^4C(O)R^5$, $NR^4C(O)OR^5$, halogen, cyano, nitro and oxides;
(iv) 8 to 10 membered bicyclic heteroaryl, having 1-6 heteroatoms independently selected from the group consisting of O, N and S, optionally substituted with 1-3 substituents independently selected from the group consisting of $R^4$, $OR^4$, $NR^4R^5$, $S(O)_qR^4$, $SO_2NR^4R^5$, $C(O)NR^4R^5$, $C(NR^4)R^5$, $NR^4SO_2R^5$, $C(O)R^4$, $C(O)OR^4$, $NR^4C(O)R^5$, $NR^4C(O)OR^5$, halogen, cyano, nitro and oxides;
(v) saturated and partially saturated $C_3$-$C_7$ monocyclic carbocyclic moiety optionally substituted with 1-3 substituents independently selected from the group consisting of $R^4$, $OR^4$, $NR^4R^5$, $S(O)_qR^4$, $SO_2NR^4R^5$, $C(O)NR^4R^5$, $C(NR^4)R^5$, $NR^4SO_2R^5$, $C(O)R^4$, $C(O)OR^4$, $NR^4C(O)R^5$, $NR^4C(O)OR^5$, halogen, cyano, and nitro;
(vi) saturated and partially saturated $C_5$-$C_{12}$ bicyclic carbocyclic moiety, optionally substituted with 1-3 substituents independently selected from the group consisting of $R^4$, $OR^4$, $NR^4R^5$, $S(O)_qR^4$, $SO_2NR^4R^5$, $C(O)NR^4R^5$, $C(NR^4)R^5$, $NR^4SO_2R^5$, $C(O)R^4$, $C(O)OR^4$, $NR^4C(O)R^5$, $NR^4C(O)OR^5$, halogen, cyano, and nitro;
(vii) saturated and partially saturated 5 to 7 membered monocyclic heterocyclic moiety, having 1-3 heteroatoms independently selected from the group consisting of O, N and S, optionally substituted with 1-3 substituents independently selected from the group consisting of $R^4$, $OR^4$, $NR^4R^5$, $S(O)_qR^4$, $SO_2NR^4R^5$, $C(O)NR^4R^5$, $C(NR^4)R^5$, $NR^4SO_2R^5$, $C(O)R^4$, $C(O)OR^4$, $NR^4C(O)R^5$, $NR^4C(O)OR^5$, halogen, cyano, nitro and oxides (e.g. =O, —O⁻ or —OH); or
(viii) saturated and partially saturated 7 to 12 membered bicyclic heterocyclic moiety, having 1-6 heteroatoms independently selected from the group consisting of O, N and S, optionally substituted with 1-3 substituents independently selected from the group consisting of $R^4$, $OR^4$, $NR^4R^5$, $S(O)_qR^4$, $SO_2NR^4R^5$, $C(O)NR^4R^5$, $C(NR^4)R^5$, $NR^4SO_2R^5$, $C(O)R^4$, $C(O)OR^4$, $NR^4C(O)R^5$, $NR^4C(O)OR^5$, halogen, cyano, nitro and oxides; and
each $R^1$, $R^2$, $R^3$, $R^4$, $R^5$ and Q is, independently,
(a) hydrogen,
(b) $C_1$-$C_5$ linear, branched, or cyclic alkyl, optionally substituted with 1-3 substituents independently selected from the group consisting of $C_1$-$C_5$ linear or branched alkyl, up to perhalo substituted $C_1$-$C_5$ linear or branched alkyl, $C_1$-$C_3$ alkoxy, hydroxy, carboxy, amino, $C_1$-$C_3$ alkylamino, $C_1$-$C_6$ dialkylamino, halogen, cyano, and nitro;
(c) phenyl, optionally substituted with 1-3 substituents independently selected from the group consisting of $C_1$-$C_5$ linear or branched alkyl, up to perhalo substituted $C_1$-$C_5$ linear or branched alkyl, $C_1$-$C_3$ alkoxy, hydroxy, carboxy, amino, $C_1$-$C_3$ alkylamino, $C_1$-$C_6$ dialkylamino, halogen, cyano, and nitro;
(d) 5-6 membered monocyclic heteroaryl having 1-4 heteroatoms selected from the group consisting of O, N and S or 8-10 membered bicyclic heteroaryl having 1-6 heteroatoms selected from the group consisting of O, N and S, optionally substituted with 1-3 substituents independently selected from the group consisting of $C_1$-$C_5$ linear or branched alkyl, up to perhalo substituted $C_1$-$C_5$ linear or branched alkyl, $C_1$-$C_3$ alkoxy, hydroxy, carboxy, amino, $C_1$-$C_3$ alkylamino, $C_1$-$C_6$ dialkylamino, halogen, cyano, and nitro;
(e) $C_1$-$C_3$ alkyl-phenyl, optionally substituted with 1-3 substituents independently selected from the group consisting of $C_1$-$C_5$ linear or branched alkyl, up to perhalo substituted $C_1$-$C_5$ linear or branched alkyl, $C_1$-$C_3$ alkoxy, hydroxy, carboxy, amino, $C_1$-$C_3$ alkylamino, $C_1$-$C_6$ dialkylamino, halogen, cyano, and nitro;
(f) $C_1$-$C_3$ heteroaryl-alkyl having 1-4 heteroatoms selected from the group consisting of O, N and S, wherein said heteroaryl group is a 5-6 membered monocyclic heteroaryl or a 8-10 membered bicyclic heteroaryl, optionally substituted with 1-3 substituents independently selected from the group consisting of $C_1$-$C_5$ linear or branched alkyl, up to perhalo substituted $C_1$-$C_5$ linear or branched alkyl, $C_1$-$C_3$ alkoxy, hydroxy, carboxy, amino, $C_1$-$C_3$ alkylamino, $C_1$-$C_6$ dialkylamino, halogen, cyano, and nitro; or
(g) up to per-halo substituted $C_1$-$C_5$ linear, branched or cyclic alkyl and when not perhalo substituted, optionally substituted with 1-3 substituents independently selected from the group consisting of $C_1$-$C_5$ linear or branched alkyl, up to perhalo substituted $C_1$-$C_5$ linear or branched alkyl, $C_1$-$C_3$ alkoxy, hydroxy, carboxy, amino, $C_1$-$C_3$ alkylamino, $C_1$-$C_6$ dialkylamino, halogen, cyano, and nitro.

2. A compound of formula I,

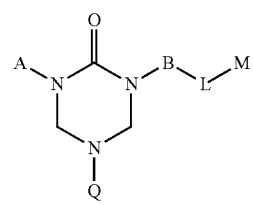

or a pharmaceutically acceptable salt thereof,
wherein B is
(i) phenyl or naphthyl, optionally substituted with 1-3 substituents independently selected from the group consisting of $C_1$-$C_5$ linear or branched alkyl, $C_1$-$C_5$ linear or branched haloalkyl up to perhalo, $C_1$-$C_3$ alkoxy, $C_1$-$C_3$ haloalkoxy up to per haloalkoxy, hydroxy, amino, $C_1$-$C_3$ alkylamino, $C_1$-$C_6$ dialkylamino, cyano, and nitro;
A is a 5-10 membered cyclic moiety which is optionally substituted with 1-4 substituents independently selected from the group consisting of $R^1$, $OR^1$, $NR^1R^2$, $S(O)_pR^1$, $SO_2NR^1R^2$, $C(O)NR^1R^2$, $C(NR^1)R^2$, $NR^1SO_2R^2$, $C(O)R^1$, $C(O)OR^1$, $NR^1C(O)R^2$, $NR^1C(O)OR^2$, cyano, and nitro, and A is additionally $C_3$ to $C_6$ linear or branched alkyl;

L is a bridging group selected from the group consisting of:
(a) —$(CH_2)_m$—O—$(CH_2)_l$—,
(b) —$(CH_2)_m$—$(CH_2)_l$—,
(c) —$(CH_2)_m$—C(O)—$(CH_2)_l$—,
(d) —$(CH_2)_m$—$NR^3$—$(CH_2)_l$—,
(e) —$(CH_2)_m$—$NR^3$C(O)—$(CH_2)_l$—,
(f) —$(CH_2)_m$—S—$(CH_2)_l$—,
(g) —$(CH_2)_m$—C(O)$NR^3$—$(CH_2)_l$—,
(h) —$(CH_2)_m$—$CF_2$—$(CH_2)_l$—,
(i) —$(CH_2)_m$—$CCl_2$—$(CH_2)_l$—,
(j) —$(CH_2)_m$—CHF—$(CH_2)_l$—,
(k) —$(CH_2)_m$—CH(OH)—$(CH_2)_l$—;
(l) —$(CH_2)_m$—C≡C—$(CH_2)_l$; and
(m);
wherein m and l are integers independently selected from 0-4, M is
(i) phenyl, optionally substituted with 1-3 substituents independently selected from the group consisting of $R^4$, $OR^4$, $NR^4R^5$, $S(O)_qR^4$, $SO_2NR^4R^5$, $C(O)NR^4R^5$, $C(NR^4)R^5$, $NR^4SO_2R^5$, $C(O)R^4$, $C(O)OR^4$, $NR^4C(O)R^5$, $NR^4C(O)OR^5$, halogen, cyano, and nitro;
(ii) naphthyl, optionally substituted with 1-3 substituents independently selected from the group consisting of $R^4$, $OR^4$, $NR^4R^5$, $S(O)_qR^4$, $SO_2NR^4R^5$, $C(O)NR^4R^5$, $C(NR^4)R^5$, $NR^4SO_2R^5$, $C(O)R^4$, $C(O)OR^4$, $NR^4C(O)R^5$, $NR^4C(O)OR^5$, halogen, cyano, and nitro;
(iii) 5 and 6 membered monocyclic heteroaryl, having 1-3 heteroatoms independently selected from the group consisting of O, N and S, optionally substituted with 1-3 substituents independently selected from the group consisting $R^4$, $OR^4$, $NR^4R^5$, $S(O)_qR^4$, $SO_2NR^4R^5$, $C(O)NR^4R^5$, $C(NR^4)R^5$, $NR^4SO_2R^5$, $C(O)R^4$, $C(O)OR^4$, $NR^4C(O)R^5$, $NR^4C(O)OR^5$, halogen, cyano, nitro and oxides;
(iv) 8 to 10 membered bicyclic heteroaryl, having 1-6 heteroatoms independently selected from the group consisting of O, N and S, optionally substituted with 1-3 substituents independently selected from the group consisting of $R^4$, $OR^4$, $NR^4R^5$, $S(O)_qR^4$, $SO_2NR^4R^5$, $C(O)NR^4R^5$, $C(NR^4)R^5$, $NR^4SO_2R^5$, $C(O)R^4$, $C(O)OR^4$, $NR^4C(O)R^5$, $NR^4C(O)OR^5$, halogen, cyano, nitro and oxides;
(v) saturated and partially saturated $C_3$-$C_7$ monocyclic carbocyclic moiety optionally substituted with 1-3 substituents independently selected from the group consisting of $R^4$, $OR^4$, $NR^4R^5$, $S(O)_qR^4$, $SO_2NR^4R^5$, $C(O)NR^4R^5$, $C(NR^4)R^5$, $NR^4SO_2R^5$, $C(O)R^4$, $C(O)OR^4$, $NR^4C(O)R^5$, $NR^4C(O)OR^5$, halogen, cyano, and nitro;
(vi) saturated and partially saturated $C_5$-$C_{12}$ bicyclic carbocyclic moiety, optionally substituted with 1-3 substituents independently selected from the group consisting of $R^4$, $OR^4$, $NR^4R^5$, $S(O)_qR^4$, $SO_2NR^4R^5$, $C(O)NR^4R^5$, $C(NR^4)R^5$, $NR^4SO_2R^5$, $C(O)R^4$, $C(O)OR^4$, $NR^4C(O)R^5$, $NR^4C(O)OR^5$, halogen, cyano, and nitro;
(vii) saturated and partially saturated 5 to 7 membered monocyclic heterocyclic moiety, having 1-3 heteroatoms independently selected from the group consisting of O, N and S, optionally substituted with 1-3 substituents independently selected from the group consisting of $R^4$, $OR^4$, $NR^4R^5$, $S(O)_qR^4$, $SO_2NR^4R^5$, $C(O)NR^4R^5$, $C(NR^4)R^5$, $NR^4SO_2R^5$, $C(O)R^4$, $C(O)OR^4$, $NR^4C(O)R^5$, $NR^4C(O)OR^5$, halogen, cyano, nitro and oxides (e.g. =O, —$O^-$ or —OH); or
(viii) saturated and partially saturated 7 to 12 membered bicyclic heterocyclic moiety, having 1-6 heteroatoms independently selected from the group consisting of O, N and S, optionally substituted with 1-3 substituents independently selected from the group consisting of $R^4$, $OR^4$, $NR^4R^5$, $S(O)_qR^4$, $SO_2NR^4R^5$, $C(O)NR^4R^5$, $C(NR^4)R^5$, $NR^4SO_2R^5$, $C(O)R^4$, $C(O)OR^4$, $NR^4C(O)R^5$, $NR^4C(O)OR^5$, halogen, cyano, nitro and oxides; and each R1, $R^2$, $R^3$, $R^4$, $R^5$ and Q is, independently,
(a) hydrogen,
(b) $C_1$-$C_5$ linear, branched, or cyclic alkyl, optionally substituted with 1-3 substituents independently selected from the group consisting of $C_1$-$C_5$ linear or branched alkyl, up to perhalo substituted $C_1$-$C_5$ linear or branched alkyl, $C_1$-$C_3$ alkoxy, hydroxy, carboxy, amino, $C_1$-$C_3$ alkylamino, $C_1$-$C_6$ dialkylamino, halogen, cyano, and nitro;
(c) phenyl, optionally substituted with 1-3 substituents independently selected from the group consisting of $C_1$-$C_5$ linear or branched alkyl, up to perhalo substituted $C_1$-$C_5$ linear or branched alkyl, $C_1$-$C_3$ alkoxy, hydroxy, carboxy, amino, $C_1$-$C_3$ alkylamino, $C_1$-$C_6$ dialkylamino, halogen, cyano, and nitro;
(d) 5-6 membered monocyclic heteroaryl having 1-4 heteroatoms selected from the group consisting of O, N and S or 8-10 membered bicyclic heteroaryl having 1-6 heteroatoms selected from the group consisting of O, N and S, optionally substituted with 1-3 substituents independently selected from the group consisting of $C_1$-$C_5$ linear or branched alkyl, up to perhalo substituted $C_1$-$C_5$ linear or branched alkyl, $C_1$-$C_3$ alkoxy, hydroxy, carboxy, amino, $C_1$-$C_3$ alkylamino, $C_1$-$C_6$ dialkylamino, halogen, cyano, and nitro;
(e) $C_1$-$C_3$ alkyl-phenyl, optionally substituted with 1-3 substituents independently selected from the group consisting of $C_1$-$C_5$ linear or branched alkyl, up to perhalo substituted $C_1$-$C_5$ linear or branched alkyl, $C_1$-$C_3$ alkoxy, hydroxy, carboxy, amino, $C_1$-$C_3$ alkylamino, $C_1$-$C_6$ dialkylamino, halogen, cyano, and nitro;
(f) $C_1$-$C_3$ heteroaryl-alkyl having 1-4 heteroatoms selected from the group consisting of O, N and S, wherein said heteroaryl group is a 5-6 membered monocyclic heteroaryl or a 8-10 membered bicyclic heteroaryl, optionally substituted with 1-3 substituents independently selected from the group consisting of $C_1$-$C_5$ linear or branched alkyl, up to perhalo substituted $C_1$-$C_5$ linear or branched alkyl, $C_1$-$C_3$ alkoxy, hydroxy, carboxy, amino, $C_1$-$C_3$ alkylamino, $C_1$-$C_6$ dialkylamino, halogen, cyano, and nitro; or
(g) up to per-halo substituted $C_1$-$C_5$ linear, branched or cyclic alkyl and when not perhalo substituted, optionally substituted with 1-3 substituents independently selected from the group consisting of $C_1$-$C_5$ linear or branched alkyl, up to perhalo substituted $C_1$-$C_5$ linear or branched alkyl, $C_1$-$C_3$ alkoxy, hydroxy, carboxy, amino, $C_1$-$C_3$ alkylamino, $C_1$-$C_6$ dialkylamino, halogen, cyano, and nitro.

3. A compound as in claim 2 wherein B is phenyl, optionally substituted with 1-3 substituents independently selected from the group consisting of $C_1$-$C_5$ linear or branched alkyl, $C_1$-$C_5$ linear or branched haloalkyl, $C_1$-$C_3$ alkoxy, hydroxy, amino, $C_1$-$C_3$ alkylamino, $C_1$-$C_6$ dialkylamino, cyano, and nitro.

4. A compound as in claim 1, wherein M is optionally substituted pyridine, quinoline, morpholine, indazole, isoquinoline, pyrimidine, or benzimidazole.

5. A compound as in claim 1, wherein A is optionally substituted furyl, thienyl, thiadiazolyl, pyrrolyl, pyrazolyl, isoxazolyl, pyridyl, pyrimidyl, pyridazinyl, pyrazinyl, quinolyl, indazolyl, benzimidazolyl, phenyl, tetrahydro-4H-benzo [1,3]dioxinyl or naphthyl.

6. A compound as in claim 1, wherein A is optionally substituted furyl, thienyl, thiadiazolyl, pyrrolyl, pyrazolyl, isoxazolyl, pyridyl, pyrimidyl, pyridazinyl, pyrazinyl, quinolyl, isoquinolyl, indazolyl, benzimidazolyl, phenyl, tetrahydro-4H-benzo [1,3]dioxinyl or naphthyl, and B is optionally substituted phenyl, naphthyl, quinolyl, or pyridyl.

7. A compound as in claim 2, wherein B is optionally substituted by one or more of methyl, trifluoromethyl, ethyl, n-propyl, n-butyl, n-pentyl, i-propyl, t-butyl, methoxy, ethoxy, propoxy, cyano, nitro, hydroxy, amino, methylamino, dimethylamino, ethylamino or diethylamino.

8. A compound as in claim 1, wherein A is optionally substituted by one or more of methyl, trifluoromethyl, ethyl, n-propyl, n-butyl, n-pentyl, isopropyl, tert-butyl, sec-butyl, isobutyl, cyclopropyl, cyclobutyl, cyclopentyl, 4-methyl-phenyl, methoxy, ethoxy, propoxy, Cl, Br, F, cyano, nitro, hydroxy, amino, methylamino, dimethylamino, ethylamino or diethylamino.

9. A compound as in claim 1, where L is —O— and M is optionally substituted morpholine, pyridine, quinoline, isoquinoline, benzimidazole, indazole, or pyrimidine.

10. A compound as in claim 1, wherein
   A is optionally substituted phenyl or tetrahydro-4H-benzo [1,3]dioxinyl,
   B is phenyl or naphthyl,
   L is —O—,
   and M is optionally substituted pyridine, quinoline, isoquinoline, benzimidazole, indazole, or pyrimidine.

11. A compound as in claim 1, wherein
   A is optionally substituted pyrazolyl,
   B is phenyl or naphthyl,
   L is —(CH$_2$)$_m$—O—(CH$_2$)$_l$—, and M is morpholine.

12. A compound as in claim 1,
   wherein A is 2-(4-methyl-phenyl)-5-tert-butyl-2H-pyrazole-3-yl, B is naphthyl, L is —O—(CH$_2$)$_2$— and M is morpholine.

13. A compound as in claim 1, wherein A is 3-trifluoromethyl-4-chloro-phenyl, B is phenyl, L is —O— and M is 2-methylcarbamoyl -pyridine-4-yl.

14. A compound which is:
   1-(4-chloro-3(trifluoromethyl)phenyl)-3-(4-(2-(N-methylcarbamoyl)-4-(pyridyloxy)phenyl)-2-oxo-(1,3,5-perhydrotriazapine)
   4-{3-fluoro-4-[5-methyl-2-oxo-3-(2,2,4,4-tetrafluoro-4H-benzo[1,3]dioxin-6-yl) -[1,3,5]triazinan-1-yl]-phenoxy}-pyridine-2-carbonitrile or
   4-{3-fluoro-4-[5-methyl-2-oxo-3-(2,2,4,4-tetrafluoro-4H-benzo[1,3]dioxin-6-yl) -[1,3,5]triazinan-1-yl]-phenoxy}-pyridine-2-carboxylic acid methylamide.

15. The compound which is 1-(4-chloro-3-(trifluoromethyl)phenyl)-3-(4-(2-(N-methylcarbamoyl)-4-pyridyloxy) phenyl)-2-oxo-(1,3,5-perhydrotriazapine).

16. A pharmaceutical composition with an effective amount Of one or more compounds of claim 1 and a physiologically acceptable carrier.

17. A method for treating the following condition in humans and/or other mammals: rheumatoid arthritis
   comprising administering to a human or other mammal in need thereof a compound of claim claim 1.

18. A method for treating rheumatoid arthritis, comprising administering the compound 1-(5-tert-butyl-2-(4-methyl-phenyl)-2H-pyrazole-3-yl)-3-[4-(2-morpholinylethoxy) naphthalene-1-yl])-2-oxo-(1,3,5-perhydrotriazapine).

19. A compound of formula I:

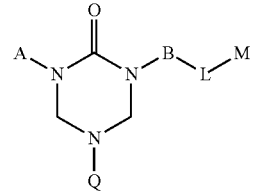

or a pharmaceutically acceptable salt thereof,
   wherein
   A of formula I is phenyl, optionally substituted with 1-3 substituents independently selected from the group consisting of R$^1$, OR$^1$, NR$^1$R$^2$, S(O)$_p$R$^1$, SO$_2$NR$^1$R$^2$, NR$^1$SO$_2$R$^2$, C(O)R$^1$, C(O)OR$^1$, C(O)NR$^1$R$^2$, NR$^1$C(O)R$^2$, NR$^1$C(O)OR$^2$, halogen, cyano, and nitro;
   B is phenyl, optionally substituted with 1-3 substituents independently selected from the group consisting of C$_1$-C$_5$ linear or branched alkyl, C$_1$-C$_5$ linear or branched haloalkyl up to perhalo, C$_1$-C$_3$ alkoxy, C$_1$-C$_3$ haloalkoxy up to per haloalkoxy, hydroxy, amino, C$_1$-C$_3$ alkylamino, C$_1$-C$_6$ dialkylamino, cyano, and nitro;
   L is —O— or —S—,
   M is phenyl, pyridine, quinoline, morpholine, indazole, isoquinoline, pyrimidine, or benzimidazole, optionally substituted with 1-3 substituents independently selected from the group consisting of R$^4$, OR$^4$, NR$^4$R$^5$, S(O)$_q$R$^4$, SO$_2$NR$^4$R$^5$, C(O)NR$^4$R$^5$, C(NR$^4$)R$^5$, NR$^4$SO$_2$R$^5$, C(O)R$^4$, C(O)OR$^4$, NR$^4$C(O)R$^5$, NR$^4$C(O)OR$^5$, halogen, cyano, and nitro;
   each R$^1$, R$^2$, R$^4$, R$^5$ and Q is independently selected from the group consisting of:
   (a) hydrogen,
   (b) C$_1$-C$_5$ linear, branched, or cyclic alkyl,
   (c) C$_1$-C$_5$ linear or branched hydroxy alkyl,
   (d) C$_1$-C$_5$ linear or branched alkoxy substituted —C$_1$-C$_5$ linear or branched alkyl,
   (e) phenyl,
   (f) pyridinyl
   (g) C$_1$-C$_3$ alkyl-phenyl,
   (h) C$_1$-C$_3$ alkyl-pyridinyl or
   (i) up to per-halo substituted C$_1$-C$_5$ linear, branched or cyclic alkyl and the variables p and q are integers independently selected from 0, 1, or 2.

20. A compound of claim 19 wherein, M is phenyl or pyridine.

21. A compound of formula I,

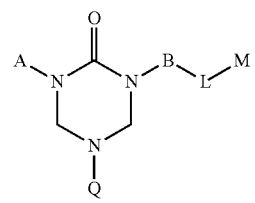

or a pharmaceutically acceptable salt thereof, wherein
   A of formula I is pyridinyl, optionally substituted with 1-3 substituents independently selected from the group consisting of R$^1$, OR, NRR$^2$, S(O)$_p$R$^1$, SO$_2$NR$^1$R$^2$, $NR^1SO_2R^2$, $C(O)R^1$, $C(O)OR^1$, $C(O)NR^1R^2$, $NR^1C(O)R^2$, $NR^1C(O)OR^2$, halogen, cyano, and nitro;

B is phenyl, optionally substituted with 1-3 substituents independently selected from the group consisting of $C_1$-$C_5$ linear or branched alkyl, $C_1$-$C_5$ linear or branched haloalkyl up to perhalo, $C_1$-$C_3$ alkoxy, $C_1$-$C_3$ haloalkoxy up to per haloalkoxy, hydroxy, amino, $C_1$-$C_3$ alkylamino, $C_1$-$C_6$ dialkylamino, cyano, and nitro;

L is —O— or —S—,

M is phenyl, pyridine, quinoline, morpholine, indazole, isoquinoline, pyrimidine, or benzimidazole, optionally substituted with 1-3 substituents which independently are $R^4$, OR, $NRR^5$, $S(O)_qR^4$, $SO_2NR^4R^5$, $C(O)NR^4R^5$, $C(NR^4)R^5$, $NR^4SO_2R^5$, $C(O)R^4$, $C(O)OR^4$, $NR^4C(O)R^5$, $NR^4C(O)OR^5$, halogen, cyano, or nitro;

each $R^1$, $R^2$, $R^4$, $R^5$ and Q is independently:
(a) hydrogen,
(b) $C_1$-$C_5$ linear, branched, or cyclic alkyl,
(c) $C_1$-$C_5$ linear or branched hydroxy alkyl,
(d) $C_1$-$C_5$ linear or branched alkoxy substituted —$C_1$-$C_5$ linear or branched alkyl,
(e) phenyl,
(f) pyridinyl
(g) $C_1$-$C_3$ alkyl-phenyl,
(h) $C_1$-$C_3$ alkyl-pyridinyl or
(i) up to per-halo substituted $C_1$-$C_5$ linear, branched or cyclic alkyl, each R is independently:
(b) $C_1$-$C_5$ linear, branched, or cyclic alkyl,
(c) $C_1$-$C_5$ linear or branched hydroxy alkyl,
(d) $C_1$-$C_5$ linear or branched alkoxy substituted —$C_1$-$C_5$ linear or branched alkyl,
(e) phenyl,
(f) pyridinyl
(g) $C_1$-$C_3$ alkyl-phenyl,
(h) $C_1$-$C_3$ alkyl-pyridinyl or
(i) up to per-halo substituted $C_1$-$C_5$ linear, branched or cyclic alkyl, and the variables p and q are integers independently selected from 0, 1, or 2.

22. A compound of claim 21 wherein M is phenyl or pyridine.

23. A compound of formula I,

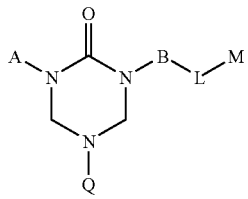

or a pharmaceutically acceptable salt thereof,
wherein
A of formula I is pyrazole, optionally substituted with 1-3 substituents independently selected from the group consisting of $R^1$, $OR^1$, $NR^1R^2$, $S(O)_pR^1$, $SO_2NR^1R^2$, $NR^1SO_2R^2$, $C(O)R^1$, $C(O)OR^1$, $C(O)NR^1R^2$, $NR^1C(O)R^2$, $NR^1C(O)OR^2$, halogen, cyano, and nitro;

B is phenyl or naphthyl, optionally substituted with 1-3 substituents independently selected from the group consisting of $C_1$-$C_5$ linear or branched alkyl, $C_1$-$C_5$ linear or branched haloalkyl up to perhalo, $C_1$-$C_3$ alkoxy, $C_1$-$C_3$ haloalkoxy up to per haloalkoxy, hydroxy, amino, $C_1$-$C_3$ alkylamino, $C_1$-$C_6$ dialkylamino, cyano, and nitro;

L is —O—or —S—,

M is phenyl, pyridine, quinoline, morpholine, indazole, isoquinoline, pyrimidine, or benzimidazole, optionally substituted with 1-3 substituents which independently are $R^4$, $OR^4$, $NR^4R^5$, $S(O)_qR^4$, $SO_2NR^4R^5$, $C(O)NR^4R^5$, $C(NR^4)R^5$, $NR^4SO_2R^5$, $C(O)R^4$, $C(O)OR^4$, $NR^4C(O)R^5$, $NR^4C(O)OR^5$, halogen, cyano, or nitro;

each $R^1$, $R^2$, $R^4$, $R^5$ and Q is independently:
(a) hydrogen,
(b) $C_1$-$C_5$ linear, branched, or cyclic alkyl,
(c) $C_1$-$C_5$ linear or branched hydroxy alkyl,
(d) $C_1$-$C_5$ linear or branched alkoxy substituted —$C_1$-$C_5$ linear or branched alkyl,
(e) phenyl,
(f) pyridinyl
(g) $C_1$-$C_3$ alkyl-phenyl,
(h) $C_1$-$C_3$ alkyl-pyridinyl or
(i) up to per-halo substituted $C_1$-$C_5$ linear, branched or cyclic alkyl and the variables p and q are integers independently selected from 0, 1, or 2.

24. A compound of claim 23 wherein M is phenyl or pyridine.

25. A compound of formula I,

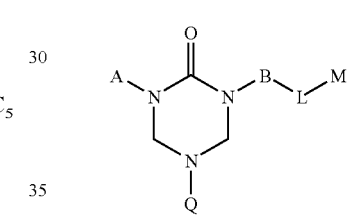

or a pharmaceutically acceptable salt thereof,
wherein
A is phenyl, optionally substituted with 1-3 substituents independently selected from the group consisting of $R^1$, $OR^1$ and halogen;

B is phenyl, optionally substituted with 1-3 substituents independently selected from the group consisting of $C_1$-$C_5$ linear or branched alkyl, $C_1$-$C_5$ linear or branched haloalkyl up to perhalo, $C_1$-$C_3$ alkoxy, $C_1$-$C_3$ haloalkoxy up to per haloalkoxy, hydroxy, amino, $C_1$-$C_3$ alkylamino, $C_1$-$C_6$ dialkylamino, cyano, and nitro;

L is —O—or —S—:

M is pyridinyl, optionally with 1-3 substituents independently selected from the group consisting $R^4$, $OR^4$, $NR^4R^5$, $S(O)_qR^4$, $SO_2NR^4R^5$, $C(O)NR^4R^5$, $C(NR^4)R^5$, $NR^4SO_2R^5$, $C(O)R^4$, $C(O)OR^4$, $NR^4C(O)R^5$, $NR^4C(O)OR^5$, halogen, cyano, nitro and oxides;

each $R^4$, $R^5$ and Q is independently:
(a) hydrogen,
(b) $C_1$-$C_5$ linear, branched, or cyclic alkyl,
(c) $C_1$-$C_5$ linear or branched hydroxy alkyl,
(d) $C_1$-$C_5$ linear or branched alkoxy substituted —$C_1$-$C_5$ linear or branched alkyl,
(e) phenyl,
(f) pyridinyl,
(g) $C_1$-$C_3$ alkyl-phenyl,
(h) $C_1$-$C_3$ alkyl-pyridinyl or
(i) up to per-halo substituted $C_1$-$C_5$ linear, branched or cyclic alkyl and the variables p and q are integers independently selected from 0, 1, or 2.

26. A compound of formula I,

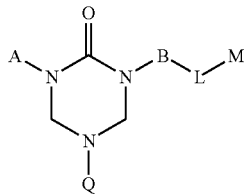

or a pharmaceutically acceptable salt thereof,
wherein
A is of the formula X:

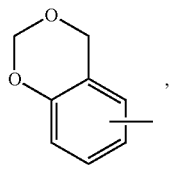

where A is optionally substituted with 1-4 substituents independently selected from the group consisting of $R^1$, $OR^1$, $NR^1R^2$, $S(O)_pR^1$, $SO_2NR^1R^2$, $NR^1SO_2R^2$, $C(O)R^1$, $C(O)OR^1$, $C(O)NR^1R^2$, $NR^1C(O)R^2$, $NR^1C(O)OR^2$, halogen, cyano, and nitro, B is phenyl, optionally substituted with 1-3 substituents independently selected from the group consisting of $C_1$-$C_5$ linear or branched alkyl, $C_1$-$C_5$ linear or branched haloalkyl up to perhalo, $C_1$-$C_3$ alkoxy, $C_1$-$C_3$ haloalkoxy up to per haloalkoxy, hydroxy, amino, $C_1$-$C_3$ alkylamino, $C_1$-$C_6$ dialkylamino, cyano, and nitro;

L is —O— or —S—:

M is:
(i) phenyl, optionally substituted with 1-3 substituents independently selected from the group consisting of $R^4$, $OR^4$, $NR^4R^5$, $S(O)_qR^4$, $SO_2NR^4R^5$, $C(O)NR^4R^5$, $C(NR^4)R^5$, $NR^4SO_2R^5$, $C(O)R^4$, $C(O)OR^4$, $NR^4C(O)R^5$, $NR^4C(O)OR^5$, halogen, cyano, and nitro; or
(ii) pyridinyl optionally with 1-3 substituents independently selected from the group consisting $R^4$, $OR^4$, $NR^4R^5$, $S(O)_qR^4$, $SO_2NR^4R^5$, $C(O)NR^4R^5$, $C(NR^4)R^5$, $NR^4SO_2R^5$, $C(O)R^4$, $C(O)OR^4$, $NR^4C(O)R^5$, $NR^4C(O)OR^5$, halogen, cyano, nitro and oxides;

where $R^4$, $R^5$ and Q are independently:
(a) hydrogen,
(b) $C_1$-$C_5$ linear, branched, or cyclic alkyl,
(c) $C_1$-$C_5$ linear or branched hydroxy alkyl,
(d) $C_1$-$C_5$ linear or branched alkoxy substituted —$C_1$-$C_5$ linear or branched alkyl,
(e) phenyl,
(f) up to per-halo substituted $C_1$-$C_5$ linear, branched or cyclic alkyl, and the variables p and q are integers independently selected from 0, 1, or 2.

27. A pharmaceutical composition with an effective amount of one or more compounds of claim 2 and a physiologically acceptable carrier.

28. A pharmaceutical composition with an effective amount of one or more compounds of claim 19 and a physiologically acceptable carrier.

* * * * *

UNITED STATES PATENT AND TRADEMARK OFFICE
CERTIFICATE OF CORRECTION

| | |
|---|---|
| PATENT NO. | : 7,928,227 B2 |
| APPLICATION NO. | : 10/788405 |
| DATED | : April 19, 2011 |
| INVENTOR(S) | : Boyer et al. |

It is certified that error appears in the above-identified patent and that said Letters Patent is hereby corrected as shown below:

Column 38, line 65 reads "$R^1$, C(O)O$R^1$, N$R^1$C(O)$R^2$, N$R^1$C(O)O$R^2$, cyano, and" should read -- $R^1$, C(O)O$R^1$, N$R^1$C(O)$R^2$, N$R^1$C(O)O$R^2$, halogen, cyano, and --

Signed and Sealed this
Sixteenth Day of October, 2012

David J. Kappos
*Director of the United States Patent and Trademark Office*